US008236835B2

(12) United States Patent
Dales et al.

(10) Patent No.: US 8,236,835 B2
(45) Date of Patent: Aug. 7, 2012

(54) HETEROCYCLIC INHIBITORS OF STEAROYL-COA DESATURASE

(75) Inventors: Natalie Dales, Arlington, MA (US); Zaihui Zhang, Vancouver (CA); Rajender Kamboj, Burnaby (CA); Jianmin Fu, Coquitlam (CA); Shaoyi Sun, Coquitlam (CA); Natalia Pokrovskaia, New Westminster (CA); Serguei Sviridov, Burnaby (CA)

(73) Assignees: Novartis AG, Basel (CH); Xenon Pharmaceuticals Inc., Burnaby (CA)

( * ) Notice: Subject to any disclaimer, the term of this patent is extended or adjusted under 35 U.S.C. 154(b) by 565 days.

(21) Appl. No.: 12/442,279

(22) PCT Filed: Sep. 19, 2007

(86) PCT No.: PCT/US2007/078854
§ 371 (c)(1),
(2), (4) Date: Mar. 20, 2009

(87) PCT Pub. No.: WO2008/036715
PCT Pub. Date: Mar. 27, 2008

(65) Prior Publication Data
US 2010/0029718 A1 Feb. 4, 2010

Related U.S. Application Data

(60) Provisional application No. 60/826,627, filed on Sep. 22, 2006.

(51) Int. Cl.
*A61K 31/426* (2006.01)
(52) U.S. Cl. ........ 514/371; 514/370; 514/365; 514/359; 514/183; 548/195; 548/194; 548/193; 548/190; 548/146
(58) Field of Classification Search .................. None
See application file for complete search history.

(56) References Cited

U.S. PATENT DOCUMENTS

| | | | | |
|---|---|---|---|---|
| 2,056,208 A * | 10/1936 | Putt | | 514/160 |
| 5,254,576 A | 10/1993 | Romine et al. | | |
| 5,670,656 A * | 9/1997 | Cox et al. | | 548/543 |
| 5,856,311 A * | 1/1999 | Camaggi et al. | | 514/3.3 |
| 6,054,435 A | 4/2000 | Or et al. | | |
| 7,767,677 B2 * | 8/2010 | Kamboj et al. | | 514/252.02 |
| 2003/0065187 A1 * | 4/2003 | Buchwald et al. | | 546/304 |
| 2003/0069266 A1 * | 4/2003 | Wang et al. | | 514/300 |
| 2004/0122016 A1 * | 6/2004 | Cao et al. | | 514/252.05 |
| 2005/0054634 A1 | 3/2005 | Busch et al. | | |
| 2005/0059726 A1 * | 3/2005 | Borthwick et al. | | 514/414 |
| 2005/0256118 A1 | 11/2005 | Altenbach et al. | | |
| 2005/0256158 A1 | 11/2005 | Ghosh et al. | | |
| 2005/0272728 A1 | 12/2005 | Altenbach et al. | | |
| 2006/0014700 A1 | 1/2006 | Cohen et al. | | |
| 2006/0041006 A1 | 2/2006 | Ibrahim et al. | | |
| 2006/0041137 A1 | 2/2006 | Cao et al. | | |
| 2008/0233163 A1 | 9/2008 | Assaf | | |
| 2008/0306121 A1 | 12/2008 | Nan et al. | | |
| 2008/0312435 A1 | 12/2008 | Saito et al. | | |

FOREIGN PATENT DOCUMENTS

| | | | |
|---|---|---|---|
| CH | 526583 | * | 9/1972 |
| CN | 1618796 A | | 5/2005 |
| EP | 0159677 A2 | | 10/1985 |
| EP | 0378791 A2 | | 7/1990 |
| EP | 0554956 A1 | | 11/1993 |
| EP | 1894930 A1 | | 3/2008 |
| EP | 1921077 A1 | | 5/2008 |
| JP | 04247076 A | | 9/1992 |
| JP | 2007-126454 A | | 5/2007 |
| WO | 9533719 A1 | | 12/1995 |
| WO | 9637466 A1 | | 11/1996 |
| WO | 98/54164 A1 | | 12/1998 |
| WO | 00/06085 A2 | | 2/2000 |
| WO | 00/34255 A1 | | 6/2000 |
| WO | 00/55168 A1 | | 9/2000 |
| WO | 02/26722 A1 | | 4/2002 |
| WO | 02/50091 A1 | | 6/2002 |
| WO | 02/064545 A1 | | 8/2002 |
| WO | 03/024962 A1 | | 3/2003 |
| WO | 03/029245 A1 | | 4/2003 |
| WO | 03/089412 A1 | | 10/2003 |
| WO | 03/099821 A1 | | 12/2003 |
| WO | 2004/032848 A2 | | 4/2004 |
| WO | 2004/080972 A1 | | 9/2004 |
| WO | 2004/089415 A2 | | 10/2004 |
| WO | 2004/089416 A2 | | 10/2004 |
| WO | 2004/089470 A2 | | 10/2004 |
| WO | 2004/092177 A1 | | 10/2004 |
| WO | 2004-096220 A1 | | 11/2004 |
| WO | 2004/100946 A1 | | 11/2004 |
| WO | 2005/002552 A2 | | 1/2005 |
| WO | 2005/044797 A1 | | 5/2005 |
| WO | 2005-061513 A1 | | 7/2005 |
| WO | 2005/075469 A1 | | 8/2005 |
| WO | 2005/085241 A1 | | 9/2005 |
| WO | 2005/089770 A1 | | 9/2005 |
| WO | 2005/089771 A1 | | 9/2005 |
| WO | 2005/090319 A1 | | 9/2005 |
| WO | 2005/100321 A1 | | 10/2005 |
| WO | 2005/105065 A2 | | 11/2005 |
| WO | 2006/020767 A2 | | 2/2006 |
| WO | 2006034315 A2 | | 3/2006 |
| WO | 2006034338 A1 | | 3/2006 |

(Continued)

OTHER PUBLICATIONS

Davies et al., "N-H Insertion reactions of rhodium carbenoids. Part 5: A convenient route to 1,3-azoles," Tetrahedron 60:3967-3977 (2004).

(Continued)

*Primary Examiner* — Anish Gupta
*Assistant Examiner* — Theodore R West
(74) *Attorney, Agent, or Firm* — Joshua Roth

(57) ABSTRACT

The present invention provides heterocyclic derivatives that modulate the activity of stearoyl-CoA desaturase. Methods of using such derivatives to modulate the activity of stearoyl-CoA desaturase and pharmaceutical compositions comprising such derivatives are also encompassed.

9 Claims, No Drawings

FOREIGN PATENT DOCUMENTS

| | | |
|---|---|---|
| WO | 2006034440 A2 | 3/2006 |
| WO | 2006/122011 A2 | 11/2006 |
| WO | 2006/122150 A1 | 11/2006 |
| WO | 2007/087429 A2 | 8/2007 |

OTHER PUBLICATIONS

Kerdesky et al., "4-Hyroxythiazole Inhibitors of 5-Lipoxygenase," J. Med. Chem. 34:2158-2165 (1991).

Meanwell et al., "Nonprostanoid Prostacyclin Mimetics, 5. Structure-Activity Relationships Associated with [3-[4(4,5-Diphenyl-2-oxazolyl)-5-oxazolyl] phenoxy]acetic Acid" J. Med. Chem. 36:3884-3903 (1993).

Nussbaumer et al., "21-23-Dithia-3, 13-diazaporphycenes—Novel Aromatic Porphycene Analogues Incorporating Thiazole," Eur. J. Org. Chem 2000:2449-2457 (2000).

Oreliana et al., "Reversible Fiber-Optic Fluorosensing of Lower Alcohols," Anal. Chem. 67:2231-2238 (1995).

Seko et al., "Synthesis and Platelet Aggregation Inhibitory Activity of Diphenylazole Derivatives. I. Thiazole and Imidazole Derivatives," Chem. Pharm. Bull 39(3):651-657 (1991).

Rose et al., "Structure-Activity Relationship (SAR): Effort Towards Blocking N-Glucuronidation of Indazoles (PF-03376056) by Human UGT1A Enzymes," Drug Metabolism Letters 3:28-34 (2009).

Weiss et al., "Firefly-Luciferin and its Analogs: A Source of new Luminescence Dyes and Ligands," Bioluminescence and Chemiluminescence: Chemistry, Biology and Applications, Proceedings of the International Symposium, 14th San Diego, CA, United States, Oct. 15-19, 2006 (2007) 247-250.

Caiku et al., "Synthesis of L-Camphorsulphonic Acid Tetrazolium Salts," Huagong Shikan (Chemical Industry Times), vol. 22, No. 3, pp. 7-9 (2008).

Padwa et al., "Several Convenient Methods for the Synthesis of 2-Amido Substituted Furans," Journal of Organic Chemistry 68(7):2609-2617 (2003).

Crawford et al., "Copper-catalyzed amidations of bromo substituted furans and thiophenes," Tetrahedron Letters 43(41):7365-7368 (Oct. 7, 2002).

* cited by examiner

HETEROCYCLIC INHIBITORS OF STEAROYL-CoA DESATURASE

This application is the National Stage of Application No. PCT/US2007/078854, filed on Sep. 19, 2007, which claims benefit under 35 U.S.C. §119(e) of U.S. Provisional Application No. 60/826,627, filed Sep. 22, 2006, the contents of which are incorporated herein by reference in their entirety.

The present invention relates generally to the field of inhibitors of stearoyl-CoA desaturase, such as heterocyclic derivatives, and uses for such compounds in treating and/or preventing various human diseases, including those mediated by stearoyl-CoA desaturase (SCD) enzymes, preferably SCD1, especially diseases related to elevated lipid levels, cardiovascular disease, diabetes, obesity, metabolic syndrome, dermatological disorders and the like.

BACKGROUND OF THE INVENTION

Acyl desaturase enzymes catalyze the formation of a double bond in fatty acids derived from either dietary sources or de novo synthesis in the liver. In mammals, at least three fatty acid desaturases exists, each with differing specificity: delta-9, delta-6, and delta-5, which introduce a double bond at the 9-10, 6-7, and 5-6 positions respectively.

Stearoyl-CoA desaturases (SCDs) act with cofactors (other agents) such as NADPH, cytochrome b5, cytochrome b5 reductase, Fe, and molecular $O_2$ to introduce a double bond into the C9-C10 position (delta 9) of saturated fatty acids, when conjugated to Coenzyme A (CoA). The preferred substrates are palmitoyl-CoA (16:0) and stearoyl-CoA (18:0), which are converted to palmitoleoyl-CoA (16:1) and oleyl-CoA (18:1), respectively. The resulting mono-unsaturated fatty acids are substrates for further metabolism by fatty acid elongases or incorporation into phospholipids, triglycerides, and cholesterol esters. A number of mammalian SCD genes have been cloned. For example, two genes have been identified in humans (hSCD1 and hSCD5) and four SCD genes have been isolated from mouse (SCD1, SCD2, SCD3, and SCD4). While the basic biochemical role of SCD has been known in rats and mice since the 1970s (Jeffcoat, R. et al., *Eur. J. Biochem.* (1979), Vol. 101, No. 2, pp. 439-445; de Antueno, R. et al., *Lipids* (1993), Vol. 28, No. 4, pp. 285-290), it has only recently been directly implicated in human disease processes.

The two human SCD genes have been previously described: hSCD1 by Brownlie et al, PCT published patent application, WO 01/62954, the disclosure of which is hereby incorporated by reference in its entirety, and hSCD2 by Brownlie, PCT published patent application, WO 02/26944, incorporated herein by reference in its entirety.

To date, the only small-molecule, drug-like compounds known that specifically inhibit or modulate SCD activity are found in the following PCT Published Patent Applications: WO 06/034338, WO 06/034446, WO 06/034441, WO 06/034440, WO 06/034341, WO 06/034315, WO 06/034312, WO 06/034279, WO 06/014168, WO 05/011657, WO 05/011656, WO 05/011655, WO 05/011654, WO 05/011653, WO 06/130986, WO 07/009,236, WO 06/086447, WO 06/101521, WO 06/125178, WO 06/125179, WO 06/125180, WO 06/125181, WO 06/125194, WO 07/044,085, WO 07/046,867, WO 07/046,868, WO 07/050,124, WO 07/056,846 and WO 07/071,023. SCD inhibitors have also been described in the following publications: Zhao et al. "Discovery of 1-(4-phenoxypiperidin-1-yl)-2-arylaminoethanone stearoyl CoA desaturase 1 inhibitors", *Biorg. Med. Chem. Lett.*, (2007), 17(12), 3388-3391 and Liu et al. "Discovery of potent, orally bioavailable stearoyl-CoA desaturase 1 inhibitors", *J. Med. Chem.*, (2007), 50(13), 3086-3100. Before the discovery of the above compounds, only certain long-chain hydrocarbons, analogs of the substrate stearic acid, had been used to study SCD activity. Known examples include thia-fatty acids, cyclopropenoid fatty acids, and certain conjugated linoleic acid isomers. Specifically, cis-12, trans-10 conjugated linoleic acid is believed to inhibit SCD enzyme activity and reduce the abundance of SCD1 mRNA, while cis-9, trans-11 conjugated linoleic acid does not. Cyclopropenoid fatty acids, such as those found in stercula and cotton seeds, are also known to inhibit SCD activity. For example, sterculic acid (8-(2 octylcyclopropenyl)octanoic acid) and malvalic acid (7-(2-oclylcyclopropenyl)heptanoic acid) are C18 and C16 derivatives of sterculoyl and malvaloyl fatty acids, respectively, having cyclopropene rings at their C9-C10 position. These agents must be coupled to CoA to act as inhibitors, and are believed to inhibit SCD enzymatic activity by direct interaction with the enzyme complex, thus inhibiting delta-9 desaturation. Other agents that may inhibit SCD activity include thia-fatty acids, such as 9-thiastearic acid (also called 8-nonylthiooctanoic acid) and other fatty acids.

There is a major unmet need for small molecule inhibitors of SCD enzyme activity because compelling evidence now exists that SCD activity is directly implicated in common human disease processes: See e.g., Attie, A. D. et al, "Relationship between stearoyl-CoA desaturase activity and plasma triglycerides in human and mouse hypertriglyceridemia", *J. Lipid Res.* (2002), Vol. 43, No. 11, pp. 1899-907; Cohen, P. et al., "Role for stearoyl-CoA desaturase-1 in leptin mediated weight loss", *Science* (2002), Vol. 297, No. 5579, pp. 240-3, Ntambi, J. M. et al., "Loss of stearoyl-CoA desaturase-1 function protects mice against adiposity", *Proc. Natl. Acad. Sci. U.S.A.* (2002), Vol. 99, No. 7, pp. 11482-6.

The present invention solves this problem by presenting new drug-like classes of compounds that are useful in modulating SCD activity and regulating lipid levels, especially plasma lipid levels, and which are useful in the treatment of SCD-mediated diseases such as diseases related to dyslipidemia and disorders of lipid metabolism, especially diseases related to elevated lipid levels, cardiovascular disease, diabetes, obesity, metabolic syndrome and the like.

SUMMARY OF THE INVENTION

The present invention provides heterocyclic derivatives that modulate the activity of stearoyl-CoA desaturase. Methods of using such derivatives to modulate the activity of stearoyl-CoA desaturase and pharmaceutical compositions comprising such derivatives are also encompassed.

Accordingly, in one aspect, the invention provides compounds of formula (I):

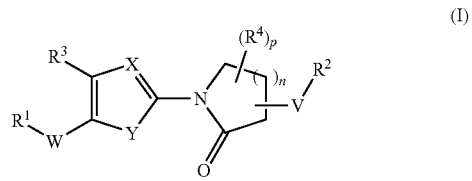

X is CH or N;
Y is NH, N—CH$_3$, O or S;
W is selected from —N(R$^5$)C(O)—, —C(O)N(R$^5$)—, —OC(O)N(R$^5$)—, —N(R$^5$)C(O)O—, —N(R$^5$)C(O)N(R$^5$)—, —O—, —S—, —N(R$^5$)—, —S(O)$_t$—, —N(R$^5$)S(O)$_t$—, —S(O)$_t$N(R$^5$)—, —OS(O)$_t$N(R$^5$)—, —C(O)—, —OC(O)—, —C(O)O—, —N(R$^5$)C(=N(R$^{5a}$))NR$^5$—, —N(R$^5$)((R$^{5a}$)N=)C—, —C(=N(R$^{5a}$))N(R$^5$)—, or a direct bond;

V is selected from —N(R$^5$)C(O)—, —C(O)N(R$^5$)—, —OC(O)N(R$^5$)—, —N(R$^5$)C(O)O—, —N(R$^5$)C(O)N(R$^5$)—, —O—, —S—, —N(R$^5$)—, —S(O)$_t$—, —N(R$^5$)S(O)$_t$—, —S(O)$_t$N(R$^5$)—, —OS(O)$_t$N(R$^5$)—, —C(O)—, —OC(O)—, —C(O)O—, —N(R$^5$)C(=N(R$^{5a}$))NR$^5$, —N(R$^5$)((R$^{5a}$)N=)C—, —C(=N(R$^{5a}$))N(R$^5$)—, =C(R$^5$)— or a direct bond;

n is 0, 1, 2 or 3;

p is 0 to 9;

t is 1 or 2;

R$^1$ is selected from the group consisting of hydrogen, alkyl, alkenyl, alkynyl, hydroxyalkyl, alkoxyalkyl, cycloalkyl, cycloalkylalkyl, aryl, aralkyl, heterocyclyl, heterocyclylalkyl, heteroaryl and heteroarylalkyl;

or R$^1$ is a multi-ring structure having 2 to 4 rings wherein the rings are independently selected from the group consisting of cycloalkyl, heterocyclyl, aryl and heteroaryl and where some or all of the rings may be fused to each other;

R$^2$ is selected from the group consisting of hydrogen, alkyl, alkenyl, alkynyl, hydroxyalkyl, alkoxyalkyl, cycloalkyl, cycloalkylalkyl, aryl, aralkyl, heterocyclyl, heterocyclylalkyl, heteroaryl and heteroarylalkyl;

or R$^2$ is a multi-ring structure having 2 to 4 rings wherein the rings are independently selected from the group consisting of cycloalkyl, heterocyclyl, aryl and heteroaryl and where some or all of the rings may be fused to each other;

R$^3$ is selected from the group consisting of hydrogen, alkyl, alkenyl, alkynyl, hydroxyalkyl, alkoxyalkyl, cycloalkyl, cycloalkylalkyl, heterocyclyl, aryl, aralkyl, heteroaryl, halo, haloalkyl, haloalkoxy, cyano and —N(R$^5$)$_2$;

each R$^4$ is independently selected from the group consisting of alkyl, halo, haloalkyl, haloalkoxy, hydroxyl, hydroxyalkyl, alkoxy, —N(R$^5$)$_2$, cycloalkylalkyl and aralkyl;

or two R$^4$s attached to the same carbon form an oxo while each of the remaining R$^4$s are as described above; each R$^5$ is independently selected from the group consisting of hydrogen, alkyl, aryl, heteroaryl, cycloalkyl, hydroxyalkyl, cycloalkylalkyl and aralkyl; and R$^{5a}$ is selected from the group consisting of hydrogen, alkyl, cycloalkylalkyl and cyano; or a stereoisomer, enantiomer or tautomer thereof, a pharmaceutically acceptable salt thereof, a pharmaceutical composition thereof or a prodrug thereof.

In another aspect, the invention provides methods of treating an SCD-mediated disease or condition in a mammal, preferably a human, wherein the methods comprise administering to the mammal in need thereof a therapeutically effective amount of a compound of the invention as set forth above.

In another aspect, the invention provides compounds or pharmaceutical compositions useful in treating, preventing and/or diagnosing a disease or condition relating to SCD biological activity such as the diseases encompassed by cardiovascular disorders and/or metabolic syndrome (including dyslipidemia, insulin resistance and obesity).

In another aspect, the invention provides methods of preventing or treating a disease or condition related to elevated lipid levels, such as plasma lipid levels, especially elevated triglyceride or cholesterol levels, in a patient afflicted with such elevated levels, comprising administering to said patient a therapeutically or prophylactically effective amount of a composition as disclosed herein. The present invention also relates to novel compounds having therapeutic ability to reduce lipid levels in an animal, especially triglyceride and cholesterol levels.

In another aspect, the invention provides pharmaceutical compositions comprising the compounds of the invention as set forth above, and pharmaceutically acceptable excipients. In one embodiment, the present invention relates to a pharmaceutical composition comprising a compound of the invention in a pharmaceutically acceptable carrier and in an amount effective to modulate triglyceride level, or to treat diseases related to dyslipidemia and disorders of lipid metabolism, when administered to an animal, preferably a mammal, most preferably a human patient. In an embodiment of such composition, the patient has an elevated lipid level, such as elevated plasma triglycerides or cholesterol, before administration of said compound and said compound is present in an amount effective to reduce said lipid level.

In another aspect, the invention provides methods for treating a patient for, or protecting a patient from developing, a disease or condition mediated by stearoyl-CoA desaturase (SCD), which methods comprise administering to a patient afflicted with such disease or condition, or at risk of developing such disease or condition, a therapeutically effective amount of a compound that inhibits activity of SCD in a patient when administered thereto.

In another aspect, the invention provides methods for treating a range of diseases involving lipid metabolism and/or lipid homeostasis utilizing compounds identified by the methods disclosed herein. In accordance therewith, there is disclosed herein a range of compounds having said activity, based on a screening assay for identifying, from a library of test compounds, a therapeutic agent which modulates the biological activity of said SCD and is useful in treating a human disorder or condition relating to serum levels of lipids, such as triglycerides, VLDL, HDL, LDL, and/or total cholesterol.

It is understood that the scope of the invention as it relates to compounds of formula (I) is not intended to encompass compounds which are known, including, but not limited to, any specific compounds which are disclosed and/or claimed in the following publications:

PCT Published Patent Application, WO 00/25768;
PCT Published Patent Application, WO 99/47507;
PCT Published Patent Application, WO 01/60458;
PCT Published Patent Application, WO 01/60369;
PCT Published Patent Application, WO 94/26720;
European Published Patent Application, 0 438 230;
European Published Patent Application, 1 184 442;
CA 2,114,178; and U.S. Pat. No. 5,334,328;
U.S. Pat. No. 5,310,499; and
US Published Patent Application, 2003/0127627.

DETAILED DESCRIPTION OF THE INVENTION

Definitions

Certain chemical groups named herein are preceded by a shorthand notation indicating the total number of carbon atoms that are to be found in the indicated chemical group. For example, $C_7$-$C_{12}$alkyl describes an alkyl group, as defined below, having a total of 7 to 12 carbon atoms, and $C_4$-$C_{12}$cycloalkylalkyl describes a cycloalkylalkyl group, as defined below, having a total of 4 to 12 carbon atoms. The total number of carbons in the shorthand notation does not include carbons that may exist in substituents of the group described.

Accordingly, as used in the specification and appended claims, unless specified to the contrary, the following terms have the meaning indicated:

"Alkyl" refers to a straight or branched hydrocarbon chain radical consisting solely of carbon and hydrogen atoms, containing no unsaturation, having from one to twelve carbon atoms, preferably one to eight carbon atoms or one to six carbon atoms, and which is attached to the rest of the molecule by a single bond, e.g., methyl, ethyl, n-propyl, 1-methylethyl(iso-propyl), n-butyl, n-pentyl, 1,1-dimethylethyl(t-butyl), and the like. Unless stated otherwise specifically in the specification, an alkyl group may be optionally substituted by one or more of the following groups: alkyl, alkenyl, halo, haloalkyl, cyano, aryl, cycloalkyl, heterocyclyl, heteroaryl, $-OR^{14}$, $-OC(O)-R^{14}$, $-N(R^{14})_2$, $-C(O)R^{14}$, $-C(O)OR^{14}$, $-C(O)N(R^{14})_2$, $-N(R^{14})C(O)OR^{16}$, $-N(R^{14})C(O)R^{16}$, $-N(R^{14})(S(O)_tR^{16})$ (where t is 1 to 2), $-S(O)_tOR^{16}$, $-SR^{16}$ (where t is 1 to 2), $-S(O)_tR^{16}$ (where t is 0 to 2), and $-S(O)_tN(R^{14})_2$ (where t is 1 to 2), where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{16}$ is alkyl, cycloalkyl, cycloalkylalkyl, aryl, aralkyl, heterocyclyl, heterocyclylalkyl, heteroaryl or heteroarylalkyl.

"Alkenyl" refers to a straight or branched hydrocarbon chain radical group consisting solely of carbon and hydrogen atoms, containing at least one double bond, having from two to twelve carbon atoms, preferably two to eight carbon atoms or two to six carbon atoms and which is attached to the rest of the molecule by a single bond, e.g., ethenyl, prop-1-enyl, but-1-enyl, pent-1-enyl, penta-1,4-dienyl, and the like. Unless stated otherwise specifically in the specification, an alkenyl group may be optionally substituted by one or more of the following groups: alkyl, alkenyl, halo, haloalkyl, aryl, aralkyl, cycloalkyl, cycloalkylalkyl, heterocyclyl, heterocyclylalkyl, heteroaryl, heteroarylalkyl, $-OR^{14}$ $-OC(O)-R^{14}$ $-N(R^{14})_2$, $-C(O)R^{14}$, $-C(O)OR^{14}$, $-C(O)N(R^{14})_2$, $-N(R^{14})C(O)OR^{16}$, $-N(R^{14})C(O)R^{16}$, $-N(R^{14})(S(O)_tR^{16})$ (where t is 1 to 2), $-S(O)_tOR^{16}$ (where t is 0 to 2), $-SR^{16}$, $-S(O)_tR^{16}$ (where t is 1 to 2), and $-S(O)_tN(R^{14})_2$ (where t is 1 to 2), where each $R^{14}$ is independently hydrogen, alkyl, haloalkyl, cycloalkyl, cycloalkylalkyl, aryl, aralkyl, heterocyclyl, heterocyclylalkyl, heteroaryl, or heteroarylalkyl; and each $R^{16}$ is alkyl, haloalkyl, cycloalkyl, cycloalkylalkyl, aryl, aralkyl, heterocyclyl, heterocyclylalkyl, heteroaryl, or heteroarylalkyl.

"Alkynyl" refers to a straight or branched hydrocarbon chain radical group consisting solely of carbon and hydrogen atoms, containing at least one triple bond, having from two to twelve carbon atoms, preferably two to eight carbon atoms or two to six carbon atoms and which is attached to the rest of the molecule by a single bond. Unless stated otherwise specifically in the specification, an alkynyl group may be optionally substituted by one or more of the following groups: alkyl, alkenyl, halo, haloalkyl, aryl, aralkyl, cycloalkyl, cycloalkylalkyl, heterocyclyl, heterocyclylalkyl, heteroaryl, heteroarylalkyl, $-OR^{14}$, $-OC(O)-R^{14}$ $-N(R^{14})_2$, $-C(O)R^{14}$, $-C(O)OR^{14}$, $-C(O)N(R^{14})_2$, $-N(R^{14})C(O)OR^{16}$, $-N(R^{14})C(O)R^{16}$, $-N(R^{14})(S(O)_tR^{16})$ (where t is 1 to 2), $-S(O)_tOR^{16}$ (where t is 0 to 2), $-SR^{16}$, $-S(O)_tR^{16}$ (where t is 1 to 2), and $-S(O)_tN(R^{14})_2$ (where t is 1 to 2), where each $R^{14}$ is independently hydrogen, alkyl, haloalkyl, cycloalkyl, cycloalkylalkyl, aryl, aralkyl, heterocyclyl, heterocyclylalkyl, heteroaryl, or heteroarylalky; and each $R^{16}$ is alkyl, cycloalkyl, cycloalkylalkyl, aryl, aralkyl, heterocyclyl, heterocyclylalkyl, heteroaryl or heteroarylalkyl.

"Alkylene" refers to a straight or branched divalent hydrocarbon chain consisting solely of carbon and hydrogen atoms, having from one to twelve carbon atoms, and linking the rest of the molecule to a radical group, e.g., methylene, ethylene, propylene, n-butylene, and the like. The alkylene is attached to the rest of the molecule through a single bond and to the radical group through a single bond. The points of attachment of the alkeylene to the rest of the molecule and to the radical group can be through one carbon or any two carbons within the chain. Unless stated otherwise specifically in the specification, an alkylene group may be optionally substituted by one or more of the following groups: alkyl, alkenyl, halo, haloalkyl, aryl, aralkyl, cycloalkyl, cycloalkylalkyl, heterocyclyl, heterocyclylalkyl, heteroaryl, heteroarylalkyl, $-OR^{14}$, $-OC(O)-R^{14}$, $-N(R^{14})_2$, $-C(O)R^{14}$, $-C(O)OR^{14}$, $-C(O)N(R^{14})_2$, $-N(R^{14})C(O)OR^{16}$, $-N(R^{14})C(O)R^{14}$, $-N(R^{14})(S(O)_tR^{16})$ (where t is 1 to 2), $-S(O)_tOR^{16}$ (where t is 1 to 2), $-SR^{16}$, $-S(O)_tR^{16}$ (where t is 1 to 2), and $-S(O)_tN(R^{14})_2$ (where t is 1 to 2), where each $R^{14}$ is independently hydrogen, alkyl, haloalkyl, cycloalkyl, cycloalkylalkyl, aryl, aralkyl, heterocyclyl, heterocyclylalkyl, heteroaryl, or heteroarylalkyl; and each $R^{16}$ is alkyl, haloalkyl, cycloalkyl, cycloalkylalkyl, aryl, aralkyl, heterocyclyl, heterocyclylalkyl, heteroaryl, or heteroarylalkyl.

"Alkenylene" refers to a straight or branched divalent hydrocarbon chain consisting solely of carbon and hydrogen atoms, containing at least one double bond, having from two to twelve carbon atoms, and linking the rest of the molecule to a radical group, e.g. ethenylene, propenylene, n-butenylene, and the like. The alkenylene is attached to the rest of the molecule through a single bond and to the radical group through a double bond or a single bond. The points of attachment of the alkeylene to the rest of the molecule and to the radical group can be through one carbon or any two carbons within the chain. Unless stated otherwise specifically in the specification, an alkenylene group may be optionally substituted by one or more of the following groups: alkyl, alkenyl, halo, haloalkyl, aryl, aralkyl, cycloalkyl, cycloalkylalkyl, heterocyclyl, heterocyclylalkyl, heteroaryl, heteroarylalkyl, $-OR^{14}$, $-OC(O)-R^{14}$, $-N(R^{14})_2$, $-C(O)R^{14}$, $-C(O)OR^{14}$, $-C(O)N(R^{14})_2$, $-N(R^{14})C(O)OR^{16}$, $-N(R^{14})C(O)R^{16}$, $-N(R^{14})(S(O)_tR^{16})$ (where t is 1 to 2), $-S(O)_tOR^{16}$ (where t is 1 to 2), $-SR^{16}$, $-S(O)_tR^{16}$ (where t is 1 to 2), and $-S(O)_tN(R^{14})_2$ (where t is 1 to 2) where each $R^{14}$ is independently hydrogen, alkyl, haloalkyl, cycloalkyl, cycloalkylalkyl, aryl, aralkyl, heterocyclyl, heterocyclylalkyl, heteroaryl, or heteroarylalkyl; and each $R^{16}$ is alkyl, haloalkyl, cycloalkyl, cycloalkylalkyl, aryl, aralkyl, heterocyclyl, heterocyclylalkyl, heteroaryl, or heteroarylalkyl.

"Alkynylene" refers to a straight or branched divalent hydrocarbon chain consisting solely of carbon and hydrogen atoms, containing at least one triple, having from two to twelve carbon atoms, and linking the rest of the molecule to a radical group, e.g. propynylene, n-butynylene, and the like. The alkynylene is attached to the rest of the molecule through a single bond and to the radical group through a single bond. The points of attachment of the alkynylene to the rest of the molecule and to the radical group can be through one carbon or any two carbons within the chain. Unless stated otherwise specifically in the specification, an alkynylene group may be optionally substituted by one or more of the following groups: alkyl, alkenyl, halo, haloalkyl, aryl, aralkyl, cycloalkyl, cycloalkylalkyl, heterocyclyl, heterocyclylalkyl, heteroaryl, heteroarylalkyl, $-OR^{14}$, $-OC(O)-R^{14}$, $-N(R^{14})_2$, $-C(O)R^{14}$, $-C(O)OR^{14}$, $-C(O)N(R^{14})_2$, $-N(R^{14})C(O)OR^{16}$, $N(R^{14})C(O)R^{16}$, $-N(R^{14})(S(O)_tR^{16})$ (where t is 1 to 2), $-S(O)_tOR^{16}$ (where t is 1 to 2), $-SR^{16}$, $-S(O)_tR^{16}$ (where t is 0 to 2), and —S(O)$_t$N(R$^{14}$)$_2$ (where t is 1 to 2), where each R$^{14}$ is independently hydrogen, alkyl, haloalkyl, cycloalkyl, cycloalkylalkyl, aryl, aralkyl, heterocyclyl, heterocyclylalkyl, heteroaryl, or heteroarylalkyl; and each R$^{16}$ is alkyl, haloalkyl, cycloalkyl, cycloalkylalkyl, aryl, aralkyl, heterocyclyl, heterocyclylalkyl, heteroaryl, or heteroarylalkyl.

"Alkoxy" refers to a radical of the formula —OR$_a$ where R$_a$ is an alkyl radical as generally defined above. The alkyl part of the alkoxy radical may be optionally substituted as defined above for an alkyl radical.

"Alkoxyalkyl" refers to a radical of the formula —R$_a$—O—R$_3$ where each R$_a$ is independently an alkyl radical as defined above. The oxygen atom may be bonded to any carbon in either alkyl radical. Each alkyl part of the alkoxyalkyl radical may be optionally substituted as defined above for an alkyl group.

"Aryl" refers to aromatic monocyclic or multicyclic hydrocarbon ring system consisting only of hydrogen and carbon and containing from six to nineteen carbon atoms, preferably six to ten carbon atoms, where the ring system may be partially saturated. Aryl groups include, but are not limited to groups such as fluorenyl, phenyl and naphthyl. Unless stated otherwise specifically in the specification, the term "aryl" or the prefix "ar-" (such as in "aralkyl") is meant to include aryl radicals optionally substituted by one or more substituents selected from the group consisting of alkyl, alkenyl, alkynyl, halo, haloalkyl, cyano, nitro, aryl, aralkyl, cycloalkyl, cycloalkylalkyl, heterocyclyl, heterocyclylalkyl, heteroaryl, heteroarylalkyl, —R$^{15}$—OR$^{14}$, —R$^{15}$—OC(O)—R$^{14}$, —R$^{15}$—N(R$^{14}$)$_2$, —R$^{15}$—C(O)R$^{14}$, —R$^{15}$—C(O)OR$^{14}$, —R$^{15}$—C(O)N(R$^{14}$)$_2$, —R$^{15}$—N(R$^{14}$)C(O)OR$^{16}$, —R$^{15}$—N(R$^{14}$)C(O)R$^{16}$, —R$^{15}$—N(R$^{14}$)(S(O)$_t$R$^{16}$) (where t is 1 to 2), —R$^{15}$—S(O)$_t$OR$^{16}$ (where t is 1 to 2), —R$^{15}$—SR$^{16}$, —R$^{15}$—S(O)$_t$R$^{16}$ (where t is 0 to 2), and —R$^{15}$—S(O)$_t$N(R$^{14}$)$_2$ (where t is 1 to 2), where each R$^{14}$ is independently hydrogen, alkyl, haloalkyl, cycloalkyl, cycloalkylalkyl, aryl, aralkyl, heterocyclyl, heterocyclylalkyl, heteroaryl, or heteroarylalkyl; each R$^{15}$ is independently a direct bond or a straight or branched alkylene or alkenylene chain; and each R$^{16}$ is alkyl, haloalkyl, cycloalkyl, cycloalkylalkyl, aryl, aralkyl, heterocyclyl, heterocyclylalkyl, heteroaryl, or heteroarylalkyl.

"Aralkyl" refers to a radical of the formula —R$_a$R$_b$ where R$_a$ is an alkyl radical as defined above and R$_b$ is one or more aryl radicals as defined above, e.g., benzyl, diphenylmethyl and the like. The aryl part of the aralkyl radical may be optionally substituted as described above for an aryl group. The alkyl part of the aralkyl radical may be optionally substituted as defined above for an alkyl group.

"Cycloalkyl" refers to a stable non-aromatic monocyclic or bicyclic hydrocarbon radical consisting solely of carbon and hydrogen atoms, having from three to fifteen carbon atoms, preferably having from three to twelve carbon atoms or from three to seven atoms, and which is saturated or unsaturated and attached to the rest of the molecule by a single bond, e.g., cyclopropyl, cyclobutyl, cyclopentyl, cyclohexyl, decalinyl and the like. Unless otherwise stated specifically in the specification, the term "cycloalkyl" is meant to include cycloalkyl radicals which are optionally substituted by one or more substituents selected from the group consisting of alkyl, alkenyl, alkynyl, fluoro, haloalkyl, cyano, aryl, aralkyl, cycloalkyl, cycloalkylalkyl, heterocyclyl, heterocyclylalkyl, heteroaryl, heteroarylalkyl, —R$^{15}$—OR$^{14}$, —R$^{15}$—OC(O)—R$^{14}$, —R$^{15}$—N(R$^{14}$)$_2$, —R$^{15}$—C(O)R$^{14}$, —R$^{15}$—C(O)OR$^{14}$, —R$^{15}$—C(O)N(R$^{14}$)$_2$, —R$^{15}$—N(R$^{14}$)C(O)OR$^{16}$, —R$^{15}$—N(R$^{14}$)C(O)R$^{16}$, —R$^{15}$—N(R$^{14}$)(S(O)$_t$R$^{16}$) (where t is 1 to 2), —R$^{15}$—S(O)$_t$OR$^{16}$ (where t is 1 to 2), —R$^{15}$—SR$^{16}$, —R$^{15}$—S(O)$_t$R$^{16}$ (where t is 0 to 2), and —R$^{15}$—S(O)$_t$N(R$^{14}$)$_2$ (where t is 1 to 2), where each R$^{14}$ is independently hydrogen, alkyl, haloalkyl, cycloalkyl, cycloalkylalkyl, aryl, aralkyl, heterocyclyl, heterocyclylalkyl, heteroaryl, or heteroarylalkyl; each R$^{15}$ is independently a direct bond or a straight or branched alkylene or alkenylene chain; and each R$^{16}$ is alkyl, haloalkyl, cycloalkyl, cycloalkylalkyl, aryl, aralkyl, heterocyclyl, heterocyclylalkyl, heteroaryl, or heteroarylalkyl.

"Cycloalkylalkyl" refers to a radical of the formula —R$_a$R$_d$ where R$_a$ is an alkyl radical as defined above and R$_d$ is a cycloalkyl radical as defined above. The cycloalkyl part of the cycloalkylalkyl radical may be optionally substituted as defined above for a cycloalkyl radical. The alkyl part of the cycloalkylalkyl radical may be optionally substituted as defined above for an alkyl radical.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, and the like. The alkyl part of the haloalkyl radical may be optionally substituted as defined above for an alkyl group.

"Haloalkoxy" refers to a radical of the formula —OR$^9$ where R$^9$ is a haloalkyl group as defined above. The haloalkyl group may be optionally substituted as defined above for a haloalkyl group.

"Heterocyclyl" refers to a stable 3- to 18-membered non-aromatic ring radical which consists of carbon atoms and from one to five heteroatoms selected from the group consisting of nitrogen, oxygen and sulfur. For purposes of this invention, the heterocyclyl radical may be a monocyclic, bicyclic or tricyclic ring system, which may include fused or bridged ring systems, which may be partially unsaturated; and the nitrogen, carbon or sulfur atoms in the heterocyclyl radical may be optionally oxidized; the nitrogen atom may be optionally alkylated/substituted; and the heterocyclyl radical may be partially or fully saturated. Examples of such heterocyclyl radicals include, but are not limited to, dioxolanyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl, homopiperidinyl, homopiperazinyl, and quinuclidinyl. Unless stated otherwise specifically in the specification, the term "heterocyclyl" is meant to include heterocyclyl radicals as defined above which are optionally substituted by one or more substituents selected from the group consisting of alkyl, alkenyl, halo, haloalkyl, cyano, oxo, thioxo, aryl, aralkyl, cycloalkyl, cycloalkylalkyl, heterocyclyl, heterocyclylalkyl, heteroaryl, heteroarylalkyl, —R$^{15}$—OR$^{14}$, —R$^{15}$—OC(O)—R$^{14}$, —R$^{15}$—N(R$^{14}$)$_2$—R$^{15}$—C(O)R$^{14}$, —R$^{15}$—C(O)OR$^{14}$, —R$^{15}$—C(O)N(R$^{14}$)$_2$, —R$^{15}$—N(R$^{14}$)C(O)OR$^{16}$, —R$^{15}$—N(R$^{14}$)C(O)R$^{16}$, —R$^{15}$—N(R$^{14}$)(S(O)$_t$R$^{16}$) (where t is 1 to 2), —R$^{15}$—S(O)$_t$OR$^{16}$ (where t is 1 to 2), —R$^{15}$—SR$^{16}$, —R$^{15}$—S(O)$_t$R$^{16}$ (where t is 0 to 2), and —R$^{15}$—S(O)$_t$N(R$^{14}$)$_2$ (where t is 1 to 2), where each R$^{14}$ is independently hydrogen, alkyl, haloalkyl, cycloalkyl, cycloalkylalkyl, aryl, aralkyl, heterocyclyl, heterocyclylalkyl, heteroaryl, or heteroarylalkyl; each R$^{15}$ is independently a direct bond or a straight or branched alkylene or alkenylene chain; and each R$^{16}$ is alkyl, haloalkyl, cycloalkyl, cycloalkylalkyl, aryl, aralkyl, heterocyclyl, heterocyclylalkyl, heteroaryl, or heteroarylalkyl, and where each of the above substituents is unsubstituted.

"Heterocyclylalkyl" refers to a radical of the formula —$R_aR_e$ where $R_a$ is an alkyl radical as defined above and $R_e$ is a heterocyclyl radical as defined above, and if the heterocyclyl is a nitrogen-containing heterocyclyl, the heterocyclyl may be attached to the alkyl radical at the nitrogen atom. The alkyl part of the heterocyclylalkyl radical may be optionally substituted as defined above for an alkyl group. The heterocyclyl part of the heterocyclylalkyl radical may be optionally substituted as defined above for a heterocyclyl group.

"Heteroaryl" refers to a 5- to 18-membered aromatic ring radical which consists of carbon atoms and from one to five heteroatoms selected from the group consisting of nitrogen, oxygen and sulfur. For purposes of this invention, the heteroaryl radical may be a monocyclic, bicyclic or tricyclic ring system, which may include fused or bridged ring systems, which may be partially saturated; and the nitrogen, carbon or sulfur atoms in the heteroaryl radical may be optionally oxidized; the nitrogen atom may be optionally alkylated/substituted. Examples include, but are not limited to, azepinyl, acridinyl, benzimidazolyl, benzthiazolyl, benzindolyl, benzothiadiazolyl, benzonaphthofuranyl, benzoxazolyl, benzodioxolyl, benzodioxinyl, benzopyranyl, benzopyranonyl, benzofuranyl, benzofuranonyl, benzothienyl, benzothiophenyl, benzotriazolyl, benzo[4,6]imidazo[1,2-a]pyridinyl, carbazolyl, cinnolinyl, dibenzofuranyl, furanyl, furanonyl, isothiazolyl, imidazolyl, indolyl, indazolyl, isoindolyl, indolinyl, isoindolinyl, indolizinyl, isoxazolyl, naphthyridinyl, oxadiazolyl, 2-oxoazepinyl, oxazolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, isoquinolinyl, thiazolyl, thiadiazolyl, triazolyl, tetrazolyl, triazinyl, and thiophenyl. Unless stated otherwise specifically in the specification, the term "heteroaryl" is meant to include heteroaryl radicals as defined above which are optionally substituted by one or more substituents selected from the group consisting of alkyl, alkenyl, alkynyl, halo, haloalkyl, cyano, oxo, thioxo, nitro, aryl, aralkyl, cycloalkyl, cycloalkylalkyl, heterocyclyl, heterocyclylalkyl, heteroaryl, heteroarylalkyl, —$R^{15}$—$OR^{14}$, —$R^{15}$—$OC(O)$—$R^{14}$, —$R^{15}$—$N(R^{14})_2$, —$R^{15}$—$C(O)R^{14}$, —$R^{15}$—$C(O)OR^{14}$, —$R^{15}$—$C(O)N(R^{14})_2$, —$R^{15}$—$N(R^{14})C(O)OR^{16}$, —$R^{15}$—$N(R^{14})C(O)R^{16}$, —$R^{15}$—$N(R^{14})(S(O)_tR^{16})$ (where t is 1 to 2), —$R^{15}$—$S(O)_tOR^{16}$ (where t is 1 to 2), —$R^{15}$—$SR^{16}$, —$R^{15}$—$S(O)_tR^{16}$ (where t is 0 to 2), and —$R^{15}$—$S(O)_tN(R^{14})_2$ (where t is 1 to 2), where each $R^{14}$ is independently hydrogen, alkyl, haloalkyl, cycloalkyl, cycloalkylalkyl, aryl, aralkyl, heterocyclyl, heterocyclylalkyl, heteroaryl, or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl, or heteroarylalkyl.

"Hydroxyalkyl" refers to a radical of the formula —$R_a$—OH where $R_a$ is an alkyl radical as defined above. The hydroxy group may be attached to the alkyl radical on any carbon within the alkyl radical. The alkyl part of the hydroxyalkyl group may be optionally substituted as defined above for an alkyl group.

"A multi-ring structure" refers to a multicyclic ring system comprised of two to four rings wherein the rings are independently selected from cycloalkyl, aryl, heterocyclyl or heteroaryl as defined above. Each cycloalkyl may be optionally substituted as defined above for a cycloalkyl group. Each aryl may be optionally substituted as defined above for an aryl group. Each heterocyclyl may be optionally substituted as defined above for a heterocyclyl group. Each heteroaryl may be optionally substituted as defined above for a heteroaryl group. The rings may be attached to each other through direct bonds or some or all of the rings may be fused to each other.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood or conversion in the gut or liver. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, Anglican Pharmaceutical Association arid Pergamon Press, 1987, both of which are incorporated in full by reference herein.

The term "prodrug" is also meant to include any covalently bonded carriers which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto or acid group is bonded to any group that, when the prodrug of the compound of the invention is administered to a mammalian subject, cleaves to form a free hydroxy, free amino or free mercapto or acid group, respectively. Examples of prodrugs include, but are not limited to, acetate, formate and benzoate derivatives of alcohol or amides of amine functional groups in the compounds of the invention and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphorirc acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients thereof.

"Therapeutically effective amount" refers to that amount of a compound of the invention which, when administered to a mammal, preferably a human, is sufficient to effect treatment, as defined below, of an SCD-mediated disease or condition in the mammal, preferably a human. The amount of a compound of the invention which constitutes a "therapeutically effective amount" will vary depending on the compound, the condition and its severity, and the age and body weight of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or disorder of interest, and includes: (i) preventing the disease or condition from occurring in a mammal, in particular, when such mammal is predisposed to the condition but has not yet been diagnosed as having it; (ii) inhibiting the disease or condition, i.e., arresting its development; or (iii) relieving the disease or condition, i.e., causing regression of the disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as HPLC using a chiral column. When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

The chemical naming protocol and structure diagrams used herein employ and rely on the chemical naming features as utilized by Chemdraw version 10.0 (available from Cambridgesoft Corp., Cambridge, Mass.).

Embodiments of the Invention

One embodiment of the invention is the compounds of formula (I)

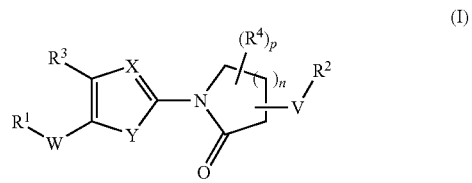

X is CH or N;
Y is NH, N—CH$_3$ O or S;

W is selected from —N(R$^5$)C(O)—, —C(O)N(R$^5$)—, —OC(O)N(R$^5$)—, —N(R$^5$)C(O)O—, —N(R$^5$)C(O)N(R$^5$)—, —O—, —S—, —N(R$^5$)—, —S(O)$_t$—, —N(R$^5$)S(O)$_t$—, —S(O)$_t$N(R$^5$)—, —OS(O)$_t$N(R$^5$)—, —C(O)—, —OC(O)—, —C(O)O—, —N(R$^5$)C(=N(R$^{5a}$))NR$^5$—, —N(R$^5$)((R$^{5a}$)N=)C—, —C(=N(R$^{5a}$))N(R$^5$)— or a direct bond;

V is selected from —N(R$^5$)C(O)—, —C(O)N(R$^5$)—, —OC(O)N(R$^5$)—, —N(R$^5$)C(O)O—, —N(R$^5$)C(O)N(R$^5$)—, —O—, —S—, —N(R$^5$)—, —S(O)$_t$—, —N(R$^5$)S(O)$_t$—, —S(O)$_t$N(R$^5$)—, —OS(O)$_t$N(R$^5$)—, —C(O)—, —OC(O)—, —C(O)O—, —N(R$^5$)C(=N(R$^{5a}$))NR$^5$—, —N(R$^5$)((R$^{5a}$)N=)C—, —C(=N(R$^{5a}$))N(R$^5$)—, =C(R$^5$)— or a direct bond;

n is 0, 1, 2 or 3;
p is 0 to 9;
t is 1 or 2;
R$^1$ is selected from the group consisting of hydrogen, alkyl, alkenyl, alkynyl, hydroxyalkyl, alkoxyalkyl, cycloalkyl, cycloalkylalkyl, aryl, aralkyl, heterocyclyl, heterocyclylalkyl, heteroaryl and heteroarylalkyl;
or R$^1$ is a multi-ring structure having 2 to 4 rings wherein the rings are independently selected from the group consisting of cycloalkyl, heterocyclyl, aryl and heteroaryl and where some or all of the rings may be fused to each other;
R$^2$ is selected from the group consisting of hydrogen, alkyl, alkenyl, alkynyl, hydroxyalkyl, alkoxyalkyl, cycloalkyl, cycloalkylalkyl, aryl, aralkyl, heterocyclyl, heterocyclylalkyl, heteroaryl and heteroarylalkyl;
or R$^2$ is a multi-ring structure having 2 to 4 rings wherein the rings are independently selected from the group consisting of cycloalkyl, heterocyclyl, aryl and heteroaryl and where some or all of the rings may be fused to each other;
R$^3$ is selected from the group consisting of hydrogen, alkyl, alkenyl, alkynyl, hydroxyalkyl, alkoxyalkyl, cycloalkyl, cycloalkylalkyl, heterocyclyl, aryl, aralkyl, heteroaryl, halo, haloalkyl, haloalkyoxy, cyano and —N(R$^5$)$_2$;
each R$^4$ is independently selected from the group consisting of alkyl, halo, haloalkyl, haloalkoxy, hydroxyl, hydroxyalkyl, alkoxy, —N(R$^5$)$_2$, cycloalkylalkyl and aralkyl;
or two R$^4$s attached to the same carbon form an oxo while each of the remaining R$^4$s are as described above;
R$^5$ is selected from the group consisting of hydrogen, alkyl, aryl, heteroaryl, cycloalkyl, hydroxyalkyl, cycloalkylalkyl and aralkyl; and
R$^{5a}$ is selected from the group consisting of hydrogen, alkyl, cycloalkylalkyl and cyano; or
a stereoisomer, enantiomer or tautomer thereof, a pharmaceutically acceptable salt thereof, a pharmaceutical composition thereof or a prodrug thereof.

A more preferred embodiment of formula (I), wherein
V is =C(R$^5$)—, —N(R$^5$)$_2$— or a direct bond;
W is —N(R$^5$)C(O)—, —C(O)N(R$^5$)—, —C(O)O— or a direct bond;
X is N or CH;
Y is S;
p is 1, 2, 3, 4, 5, 6 or 7;
R$^1$ is selected from the group consisting of hydrogen, alkyl, aryl, aralkyl, cycloalkyl, cycloalkylalkyl, heterocyclyl, heterocyclylalkyl, heteroaryl and heteroarylalkyl;
R$^2$ is selected from the group consisting of hydrogen, alkyl, alkenyl, hydroxyalkyl, alkoxyalkyl, cycloalkyl, cycloalkylalkyl, aryl, aralkyl, heterocyclyl, heterocyclylalkyl, heteroaryl and heteroarylalkyl;
R$^3$ is hydrogen or alkyl; and
R$^5$ is hydrogen or alkyl.

A more preferred embodiment of Formula I, wherein
V is a direct bond;
W is —N(R$^5$)C(O)— or —C(O)O—;
X is N or CH;
Y is S;
p is 1, 2, 3, 4, 5, 6 or 7;
R$^1$ is selected from the group consisting of alkyl, aryl, aralkyl, cycloalkylalkyl, heterocyclyl, heterocyclylalkyl and heteroarylalkyl;
R$^2$ is selected from the group consisting of hydrogen, alkyl, hydroxyalkyl, alkoxyalkyl, cycloalkyl, cycloalkylalkyl, aryl and aralkyl;
R$^3$ is hydrogen or alkyl; and
R$^5$ is hydrogen or alkyl.

A more preferred embodiment of Formula I, wherein
V is a direct bond;
W is —N(R$^5$)C(O)—;
X is N or CH;
Y is S;
p is 1, 2, 3, 4, 5, 6 or 7;
n is 1 or 2;
R$^1$ is selected from the group consisting of alkyl, aryl, aralkyl and heteroaryl;
R$^2$ is selected from the group consisting of alkyl, hydroxyalkyl, alkoxyalkyl, cycloalkyl, cycloalkylalkyl, aryl and aralkyl;
R$^3$ is alkyl; and
R$^5$ is hydrogen.

Another preferred embodiment of the invention relates to a compound of formula (I) wherein n is 1, X is N and Y is S, i.e., compound having the following formula (Ia):

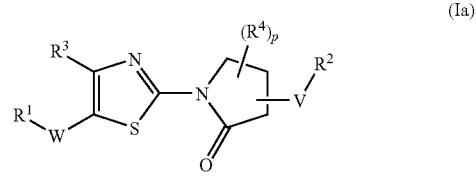

where p, W, V, R$^1$, R$^2$, R$^3$ and R$^4$ are as defined above in the Summary of the Invention.

Of this group of compounds, a subgroup of compounds are those compounds wherein:
W is —N(R$^5$)C(O)—, —C(O)N(R$^5$)—, —OC(O)N(R$^5$)—, —N(R$^5$)C(O)O—, —N(R$^5$)C(O)N(R$^5$)—, —O—, —S, —N(R$^5$)—, —S(O)$_t$—, —N(R$^5$)S(O)$_t$—, —S(O)$_t$N(R$^5$)—, —OS(O)$_t$N(R$^5$)—, —C(O)—, —OC(O)—, —C(O)O—, —N(R$^5$)C(=N(R$^{5a}$))NR$^5$, —N(R$^5$)((R$^{5a}$)N=)C—, —C(=N(R$^{5a}$))N(R$^5$)— or a direct bond;
V is —N(R$^5$)C(O)—, —C(O)N(R$^5$)—, —OC(O)N(R$^5$)—, —N(R$^5$)C(O)O—, —N(R$^5$)C(O)N(R$^5$)—, —O—, —S—, —N(R$^5$)—, —S(O)$_t$—, —N(R$^5$)S(O)$_t$—, —S(O)$_t$N(R$^5$)—, —OS(O)$_t$N(R$^5$)—, —C(O)—, —OC(O)—, —C(O)O—, —N(R$^5$)C(=N(R$^{5a}$))NR$^5$, —N(R$^5$)((R$^{5a}$)N=)C—, —C(=N(R$^{5a}$))N(R$^5$)—,
=C(R$^5$)— or a direct bond;
p is 0 to 5;
t is 1 or 2;
R$^1$ is selected from the group consisting of hydrogen, alkyl, alkenyl, alkynyl, hydroxyalkyl, alkoxyalkyl, cycloalkyl, cycloalkylalkyl, aryl, aralkyl, heterocyclyl, heterocyclylalkyl, heteroaryl and heteroarylalkyl;
R$^2$ is selected from the group consisting of hydrogen, alkyl, alkenyl, alkynyl, hydroxyalkyl, alkoxyalkyl, cycloalkyl, cycloalkylalkyl, aryl, aralkyl, heterocyclyl, heterocyclylalkyl, heteroaryl and heteroarylalkyl;
R$^3$ is selected from the group consisting of hydrogen, alkyl, alkenyl, alkynyl, hydroxyalkyl, alkoxyalkyl, cycloalkyl, cycloalkylalkyl, heterocyclyl, aryl, aralkyl, heteroaryl, halo, haloalkyl, haloalkyoxy, cyano and —N(R$^5$)$_2$;
each R$^4$ is independently selected from the group consisting of alkyl, halo, haloalkyl, haloalkoxy, hydroxyl, hydroxyalkyl, alkoxy, —N(R$^5$)$_2$, cycloalkylalkyl and aralkyl;
or two R$^4$s attached to the same carbon form an oxo while each of the remaining R$^4$s are as described above;
each R$^5$ is independently selected from the group consisting of hydrogen, alkyl, aryl, heteroaryl, cycloalkyl, hydroxyalkyl, cycloalkylalkyl and aralkyl; and
R$^{5a}$ is selected from the group consisting of hydrogen, alkyl, cycloalkylalkyl, and cyano.
Of this subgroup, a set of compounds are those compounds wherein:
W is —N(R$^5$)C(O)— or —N(R$^5$)S(O)$_t$—;
V is a direct bond or —N(R$^5$)—;
p is 0, 1, 2, 3, 4 or 5;
t is 1 or 2;
R$^1$ is selected from the group consisting of hydrogen, alkyl, alkenyl, alkynyl, hydroxyalkyl, alkoxyalkyl, cycloalkyl, cycloalkylalkyl, aryl, aralkyl, heterocyclyl, heterocyclylalkyl, heteroaryl and heteroarylalkyl;
R$^2$ is selected from the group consisting of hydrogen, alkyl, alkenyl, alkynyl, hydroxyalkyl, alkoxyalkyl, cycloalkyl, cycloalkylalkyl, aryl, aralkyl, heterocyclyl, heterocyclylalkyl, heteroaryl and heteroarylalkyl;
R$^3$ is selected from the group consisting of hydrogen, alkyl, alkenyl, alkynyl, hydroxyalkyl, alkoxyalkyl, cycloalkyl, cycloalkylalkyl, heterocyclyl, aryl, aralkyl, heteroaryl, halo, haloalkyl, haloalkyoxy, cyano and —N(R$^5$)$_2$;
each R$^4$ is independently selected from the group consisting of alkyl, halo, haloalkyl, haloalkoxy, hydroxyl, hydroxyalkyl, alkoxy, —N(R$^5$)$_2$, cycloalkylalkyl and aralkyl;
or two R$^4$s attached to the same carbon form an oxo while each of the remaining R$^4$s are as described above; and
each R$^5$ is independently selected from the group consisting of hydrogen, alkyl, aryl, heteroaryl, cycloalkyl, hydroxyalkyl, cycloalkylalkyl and aralkyl; Of this set of compounds, a subset of compounds are those compounds wherein:
W is —N(H)C(O)—;
V is a direct bond or —N(H)—;
p is 0, 1, 2, 3, 4 or 5;
R$^1$ is aralkyl or heteroarylalkyl;
R$^2$ is hydrogen, cycloalkylalkyl, aryl, aralkyl, heteroaryl or heteroarylalkyl;
R$^3$ is hydrogen or alkyl; and
each R$^4$ is independently alkyl, hydroxyl or halo.
A further preferred embodiment of the invention relates to a compound of formula (I) wherein n is 2, X is N and Y is S, i.e., compound having the following formula (Ib):

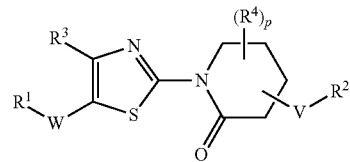

(Ib)

where p, W, V, R$^1$, R$^2$, R$^3$ and R$^4$ are as defined above in the Summary of the Invention.
Of this group of compounds, a subgroup of compounds are those compounds wherein:
W is —N(R$^5$)C(O)—, —C(O)N(R$^5$)—, —OC(O)N(R$^5$)—, —N(R$^5$)C(O)O—, —N(R$^5$)C(O)N(R$^5$)—, —O—, —S, —N(R$^5$)—, —S(O)$_t$—, —N(R$^5$)S(O)$_t$—, —S(O)$_t$N(R$^5$)—, —OS(O)$_t$N(R$^5$)—, —C(O)—, —OC(O)—, —C(O)O—, —N(R$^5$)C(=N(R$^{5a}$))NR$^5$, —N(R$^5$)((R$^{5a}$)N=)C—, —C(=N(R$^{5a}$))N(R$^5$)— or a direct bond;
V is —N(R$^5$)C(O)—, —C(O)N(R$^5$)—, —OC(O)N(R$^5$)—, —N(R$^5$)C(O)O—, —N(R$^5$)C(O)N(R$^5$)—, —O—, —S—, —N(R$^5$)—, —S(O)$_t$—, —N(R$^5$)S(O)$_t$—, —S(O)$_t$N(R$^5$)—, —OS(O)$_t$N(R$^5$)—, —C(O)—, —OC(O)—, —C(O)O—, —N(R$^5$)C(=N(R$^{5a}$))NR$^5$, —N(R$^5$)((R$^{5a}$)N=)C—, —C(=N(R$^{5a}$))N(R$^5$)—, =C(R$^5$)— or a direct bond;
p is 0, 1, 2, 3, 4, 5, 6 or 7;
t is 1 or 2;
R$^1$ is selected from the group consisting of hydrogen, alkyl, alkenyl, alkynyl, hydroxyalkyl, alkoxyalkyl, cycloalkyl, cycloalkylalkyl, aryl, aralkyl, heterocyclyl, heterocyclylalkyl, heteroaryl and heteroarylalkyl;
R$^2$ is selected from the group consisting of hydrogen, alkyl, alkenyl, alkynyl, hydroxyalkyl, alkoxyalkyl, cycloalkyl, cycloalkylalkyl, aryl, aralkyl, heterocyclyl, heterocyclylalkyl, heteroaryl and heteroarylalkyl;
R$^3$ is selected from the group consisting of hydrogen, alkyl, alkenyl, alkynyl, hydroxyalkyl, alkoxyalkyl, cycloalkyl, cycloalkylalkyl, heterocyclyl, aryl, aralkyl, heteroaryl, halo, haloalkyl, haloalkoxy, cyano and —N(R$^5$)$_2$;
each R$^4$ is independently selected from the group consisting of alkyl, halo, haloalkyl, haloalkoxy, hydroxyl, hydroxyalkyl, alkoxy, —N(R$^5$)$_2$, cycloalkylalkyl and aralkyl;
R$^5$ is selected from the group consisting of hydrogen, alkyl, aryl, heteroaryl, cycloalkyl, hydroxyalkyl, cycloalkylalkyl, and aralkyl; and
R$^{5a}$ is selected from the group consisting of hydrogen, alkyl, cycloalkylalkyl, and cyano.
Of this subgroup, a set of compounds are those compounds wherein:
W is —N(R$^5$)C(O)— or —N(R$^5$)S(O)$_t$—;
V is a direct bond, —N(R$^5$)— or =C(R$^5$)—;
p is 0, 1, 2, 3, 4, 5, 6 or 7;
t is 1 or 2;
R$^1$ is selected from the group consisting of hydrogen, alkyl, alkenyl, alkynyl, hydroxyalkyl, alkoxyalkyl, cycloalkyl, cycloalkylalkyl, aryl, aralkyl, heterocyclyl, heterocyclylalkyl, heteroaryl and heteroarylalkyl;
R$^2$ is selected from the group consisting of hydrogen, alkyl, alkenyl, alkynyl, hydroxyalkyl, alkoxyalkyl, cycloalkyl, cycloalkylalkyl, aryl, aralkyl, heterocyclyl, heterocyclylalkyl, heteroaryl and heteroarylalkyl;
R$^3$ is selected from the group consisting of hydrogen, alkyl, alkenyl, alkynyl, hydroxyalkyl, alkoxyalkyl, cycloalkyl, cycloalkylalkyl, heterocyclyl, aryl, aralkyl, heteroaryl, halo, haloalkyl, haloalkoxy, cyano, and —N($R^5$)$_2$;

each $R^4$ is independently selected from the group consisting of alkyl, halo, haloalkyl, haloalkoxy, hydroxyl, hydroxyalkyl, alkoxy, —N($R^5$)$_2$, cycloalkylalkyl and aralkyl;

or two $R^4$s attached to the same carbon form an oxo while each of the remaining $R^4$s are as described above; and $R^5$ is selected from the group consisting of hydrogen, alkyl, aryl, heteroaryl, cycloalkyl, hydroxyalkyl, cycloalkylalkyl and aralkyl.

Of this set of compounds, a subset of compounds are those compounds wherein:

W is —N(H)C(O)—;
V is a direct bond, —N(H)— or =C(H)—;
p is 0, 1, 2, 3, 4 or 5;
$R^1$ is aralkyl or heteroarylalkyl;
$R^2$ is hydrogen, cycloalkylalkyl, aryl, aralkyl, heteroaryl or heteroarylalkyl;
$R^3$ is hydrogen or alkyl; and
each $R^4$ is independently alkyl, hydroxyl, oxo or halo;
or two $R^4$s attached to the same carbon form an oxo while each of the remaining $R^4$s are as described above.

In one embodiment, the methods of the invention are directed towards the treatment and/or prevention of diseases mediated by stearoyl-CoA desaturase (SCD), especially human SCD (hSCD), preferably diseases related to dyslipidemia and disorders of lipid metabolism, and especially a disease related to elevated plasma lipid levels, cardiovascular disease, diabetes, obesity, metabolic syndrome, dermatological disorders and the like by administering an effective amount of a compound of the invention.

The present invention also relates to pharmaceutical composition containing the compounds of the invention. In one embodiment, the invention relates to a composition comprising compounds of the invention in a pharmaceutically acceptable carrier and in an amount effective to modulate triglyceride level or to treat diseases related to dyslipidemia and disorders of lipid metabolism, when administered to an animal, preferably a mammal, most preferably a human patient. In an embodiment of such composition, the patient has an elevated lipid level, such as elevated triglycerides or cholesterol, before administration of said compound of the invention and the compound of the invention is present in an amount effective to reduce said lipid level.

Utility and Testing of the Compounds Of The Invention

The present invention relates to compounds, pharmaceutical compositions and methods of using the compounds and pharmaceutical compositions for the treatment and/or prevention of diseases mediated by stearoyl-CoA desaturase (SCD), especially human SCD (hSCD), preferably diseases related to dyslipidemia and disorders of lipid metabolism, and especially a disease related to elevated plasma lipid levels, especially cardiovascular disease, diabetes, obesity, metabolic syndrome, dermatological disorders and the like, by administering to a patient in need of such treatment an effective amount of an SCD modulating, especially inhibiting, agent.

In general, the present invention provides a method for treating a patient for, or protecting a patient from developing, a disease related to dyslipidemia and/or a disorder of lipid metabolism, wherein lipid levels in an animal, especially a human being, are outside the normal range (i.e., abnormal lipid level, such as elevated plasma lipid levels), especially levels higher than normal, preferably where said lipid is a fatty acid, such as a free or complexed fatty acid, triglycerides, phospholipids, or cholesterol, such as where LDL-cholesterol levels are elevated or HDL-cholesterol levels are reduced, or any combination of these, where said lipid-related condition or disease is an SCD-mediated disease or condition, comprising administering to an animal, such as a mammal, especially a human patient, a therapeutically effective amount of a compound of the invention or a pharmaceutical composition comprising a compound of the invention wherein the compound modulates the activity of SCD, preferably human SCD1.

The compounds of the invention modulate, preferably inhibit, the activity of human SCD enzymes, especially human SCD1.

The general value of the compounds of the invention in modulating, especially inhibiting, the activity of SCD can be determined using the assay described below in Example 12.

Alternatively, the general value of the compounds in treating disorders and diseases may be established in industry standard animal models for demonstrating the efficacy of compounds in treating obesity, diabetes or elevated triglyceride or cholesterol levels or for improving glucose tolerance. Such models include Zucker obese fa/fa rats (available from Harlan Sprague Dawley, Inc. (Indianapolis, Ind.)), or the Zucker diabetic fatty rat (ZDF/GmiCrl-fa/fa) (available from Charles River Laboratories (Montreal, Quebec)), and Sprague Dawley rats (Charles Rivers), as used in models for diet-induced obesity (Ghibaudi, L. et al, (2002), *Obes. Res.* Vol. 10, pp. 956-963). Similar models have also been developed for mice and Lewis rat.

The compounds of the instant invention are inhibitors of delta-9 desaturases and are useful for treating diseases and disorders in humans and other organisms, including all those human diseases and disorders which are the result of aberrant delta-9 desaturase biological activity or which may be ameliorated by modulation of delta-9 desaturase biological activity.

As defined herein, an SCD-mediated disease or condition is defined as any disease or condition in which the activity of SCD is elevated and/or where inhibition of SCD activity can be demonstrated to bring about symptomatic improvements for the individual so treated. As defined herein, an SCD-mediated disease or condition includes, but is not limited to, a disease or condition which is, or is related to, cardiovascular disease, dyslipidemias (including but not limited to disorders of serum levels of triglycerides, hypertriglyceridemia, VLDL, HDL, LDL, fatty acid Desaturation Index (e.g. the ratio of 18:1/18:0 fatty acids, or other fatty acids, as defined elsewhere herein), cholesterol, and total cholesterol, hypercholesterolemia, as well as cholesterol disorders (including disorders characterized by defective reverse cholesterol transport)), familial combined hyperlipidemia, coronary artery disease, atherosclerosis, heart disease, cerebrovascular disease (including but not limited to stroke, ischemic stroke and transient ischemic attack (TIA)), peripheral vascular disease, and ischemic retinopathy.

An SCD-mediated disease or condition also includes metabolic syndrome (including but not limited to dyslipidemia, obesity and insulin resistance, hypertension, microalbuminemia, hyperuricaemia, and hypercoagulability), Syndrome X, diabetes, insulin resistance, decreased glucose tolerance, non-insulin-dependent diabetes mellitus, Type II diabetes, Type I diabetes, diabetic complications, body weight disorders (including but not limited to obesity, overweight, cachexia and anorexia), weight loss, body mass index and leptin-related diseases. In a preferred embodiment, compounds of the invention will be used to treat diabetes mellitus and/or obesity.

As used herein, the term "metabolic syndrome" is a recognized clinical term used to describe a condition comprising combinations of Type II diabetes, impaired glucose tolerance, insulin resistance, hypertension, obesity, increased abdominal girth, hypertriglyceridemia, low HDL, hyperuricaemia, hypercoagulability and/or microalbuminemia. The American Heart Association has published guidelines for the diagnosis of metabolic syndrome, Grundy, S., et. al., (2006) *Cardiol. Rev.* Vol. 13, No. 6, pp. 322-327.

An SCD-mediated disease or condition also includes fatty liver, hepatic steatosis, hepatitis, non-alcoholic hepatitis, non-alcoholic steatohepatitis (NASH), alcoholic hepatitis, acute fatty liver, fatty liver of pregnancy, drug-induced hepatitis, erythrohepatic protoporphyria, iron overload disorders, hereditary hemochromatosis, hepatic fibrosis, hepatic cirrhosis, hepatoma and conditions related thereto.

An SCD-mediated disease or condition also includes but is not limited to a disease or condition which is, or is related to primary hypertriglyceridemia, or hypertriglyceridemia secondary to another disorder or disease, such as hyperlipoproteinemias, familial histiocytic reticulosis, lipoprotein lipase deficiency, apolipoprotein deficiency (such as ApoCII deficiency or ApoE deficiency), and the like, or hypertriglyceridemia of unknown or unspecified etiology.

An SCD-mediated disease or condition also includes a disorder of polyunsaturated fatty acid (PUFA) disorder, or a skin disorder, including but not limited to eczema, acne, psoriasis, keloid scar formation or prevention, diseases related to production or secretions from mucous membranes, such as monounsaturated fatty acids, wax esters, and the like. Preferably, the compounds of the invention will prevent or attenuate keloid scar formation by reduction of excessive sebum production that typically results in their formation. The investigation of the role of SCD inhibitors in the treatment of acne was advanced by the discovery that rodents lacking a functional SCD1 gene had changes to the condition of their eyes, skin, coat (Zheng Y., et al. "SCD1 is expressed in sebaceous glands and is disrupted in the asebia mouse", *Nat. Genet.* (1999) 23:268-270. Miyazaki, M., "Targeted Disruption of Stearoyl-CoA Desaturasel Gene in Mice Causes Atrophy of Sebaceous and Meibomian Glands and Depletion of Wax Esters in the Eyelid", *J. Nutr.* (2001), Vol. 131, pp 2260-68., Binczek, E. et al., "Obesity resistance of the stearoyl-CoA desaturase-deficient mouse results from disruption of the epidermal lipid barrier and adaptive thermoregulation", *Biol. Chem.* (2007) Vol. 388 No. 4, pp 405-18).

An SCD-mediated disease or condition also includes inflammation, sinusitis, asthma, pancreatitis, osteoarthritis, rheumatoid arthritis, cystic fibrosis, and premenstrual syndrome.

An SCD-mediated disease or condition also includes but is not limited to a disease or condition which is, or is related to cancer, neoplasia, malignancy, metastases, tumours (benign or malignant), carcinogenesis, hepatomas and the like.

An SCD-mediated disease or condition also includes a condition where increasing lean body mass or lean muscle mass is desired, such as is desirable in enhancing performance through muscle building. Myopathies and lipid myopathies such as carnitine palmitoyltransferase deficiency (CPT I or CPT II) are also included herein. Such treatments are useful in humans and in animal husbandry, including for administration to bovine, porcine or avian domestic animals or any other animal to reduce triglyceride production and/or provide leaner meat products and/or healthier animals.

An SCD-mediated disease or condition also includes a disease or condition that is, or is related to, psychiatric disorders, multiple sclerosis, eye diseases, and immune disorders.

An SCD-mediated disease or condition also includes neurological diseases, including mild cognitive impairment, depression, schizophrenia, obsessive-compulsive disorder, and biopolar disorder.

An SCD-mediated disease or condition also includes neurodegenerative diseases, including Alzheimer's disease, Parkinson's disease, dementia with Lewy bodies, amyotrophic lateral sclerosis or Lou Gehrig's disease, Alpers' disease, Leigh's disease, Pelizaeus-Merzbacher disease, Olivopontocerebellar atrophy, Friedreich's ataxia, leukodystrophies, Rett syndrome, Ramsay Hunt syndrome type II, and Down's syndrome.

An SCD-mediated disease or condition also includes a disease or condition which is, or is related to, viral diseases or infections including but not limited to all positive strand RNA viruses, coronaviruses, SARS virus, SARS-associated coronavirus, Togaviruses, Picornaviruses, Coxsackievirus, Yellow Fever virus, Flaviviridae, ALPHAVIRUS (TOGAVIRIDAE) including Rubella virus, Eastern equine encephalitis virus, Western equine encephalitis virus, Venezuelan equine encephalitis virus, Sindbis virus, Semliki forest virus, Chikungunya virus, O'nyong'nyong virus, Ross river virus, Mayaro virus, Alphaviruses; ASTROVIRIDAE including Astrovirus, Human Astroviruses; CALICIVIRIDAE including Vesicular exanthema of swine virus, Norwalk virus, Calicivirus, Bovine calicivirus, Pig calcivirus, Hepatitis E; CORONAVIRIDAE including Coronavirus, SARS virus, Avian infectious bronchitis virus, Bovine coronavirus, Canine coronavirus, Feline infectious peritonitis virus, Human coronavirus 299E, Human coronavirus OC43, Murine hepatitis virus, Porcine epidemic diarrhea virus, Porcine hemagglutinating encephalomyelitis virus, Porcine transmissible gastroenteritis virus, Rat coronavirus, Turkey coronavirus, Rabbit coronavirus, Berne virus, Breda virus; FLAVIVIRIDAE including Hepatitis C virus, West Nile virus, Yellow Fever virus, St. Louis encephalitis virus, Dengue Group, Hepatitis G virus, Japanese B encephalitis virus, Murray Valley encephalitis virus, Central European tick-borne encephalitis virus, Far Eastern tick-borne encephalitis virus, Kyasanur forest virus, Louping ill virus, Powassan virus, Omsk hemorrhagic fever virus, Kumilinge virus, Absetarov anzalova hypr virus, ITheus virus, Rocio encephalitis virus, Langat virus, Pestivirus, Bovine viral diarrhea, Hog cholera virus, Rio Bravo Group, Tyuleniy Group, Ntaya Group, Uganda S Group, Modoc Group; PICORNAVIRIDAE including Coxsackie A virus, Rhinovirus, Hepatitis A virus, Encephalomyocarditis virus, Mengovirus, ME virus, Human poliovirus 1, Coxsackie B; POCYVIRIDAE including Potyvirus, Rymovirus, Bymovirus. Additionally it can be a disease or infection caused by or linked to Hepatitis viruses, Hepatitis B virus, Hepatitis C virus, human immunodeficiency virus (HIV) and the like. Treatable viral infections include those where the virus employs an RNA intermediate as part of the replicative cycle (hepatitis or HIV); additionally it can be a disease or infection caused by or linked to RNA negative strand viruses such as influenza and parainfluenza viruses.

The compounds identified in the instant specification inhibit the desaturation of various fatty acids (such as the $C_9$-$C_{10}$ desaturation of stearoyl-CoA), which is accomplished by delta-9 desaturases, such as stearoyl-CoA desaturase 1 (SCD1). As such, these compounds inhibit the formation of various fatty acids and downstream metabolites thereof. This may lead to an accumulation of stearoyl-CoA or palmitoyl- CoA and other upstream precursors of various fatty acids; which may possibly result in a negative feedback loop causing an overall change in fatty acid metabolism. Any of these consequences may ultimately be responsible for the overall therapeutic benefit provided by these compounds.

Typically, a successful SCD inhibitory therapeutic agent will meet some or all of the following criteria. Oral availability should be at or above 20%. Animal model efficacy is less than about 10 mg/Kg, 2 mg/Kg, 1 mg/Kg, or 0.5 mg/Kg and the target human dose is between 10 and 250 mg/70 Kg, although doses outside of this range may be acceptable. ("mg/Kg" means milligrams of compound per kilogram of body mass of the subject to whom it is being administered). The required dosage should preferably be no more than about once or twice a day or at meal times. The therapeutic index (or ratio of toxic dose to therapeutic dose) should be greater than 10. The $IC_{50}$ ("Inhibitory Concentration—50%") is a measure of the amount of compound required to achieve 50% inhibition of SCD activity, over a specific time period, in an SCD biological activity assay. Any process for measuring the activity of SCD enzymes, preferably mouse or human SCD enzymes, may be utilized to assay the activity of the compounds useful in the methods of the invention in inhibiting said SCD activity. Compounds of the invention demonstrate an $IC_{50}$ ("Inhibitory Concentration of 50%") in a 15 minute microsomal assay of preferably less than 10 µM, less than 5 µM, less than 2.5 µM, less than 1 µM, less than 750 nM, less than 500 nM, less than 250 nM, less than 100 nM, less than 50 nM, and most preferably less than 20 nM. Compounds of the invention may show reversible inhibition (i.e., competitive inhibition) and preferably do not inhibit other iron binding proteins.

The identification of compounds of the invention as SCD inhibitors was readily accomplished using the SCD enzyme and microsomal assay procedure described in Shanklin J. and Summerville C., *Proc. Natl. Acad. Sci. USA* (1991), Vol. 88, pp. 2510-2514. When tested in this assay, compounds of the invention had less than 50% remaining SCD activity at 10 µM concentration of the test compound, preferably less than 40% remaining SCD activity at 10 µM concentration of the test compound, more preferably less than 30% remaining SCD activity at 10 µM concentration of the test compound, and even more preferably less than 20% remaining SCD activity at 10 µM concentration of the test compound, thereby demonstrating that the compounds of the invention are potent inhibitors of SCD activity.

These results provide the basis for analysis of the structure-activity relationship (SAR) between test compounds and SCD. Certain-groups tend to provide more potent inhibitory compounds. SAR analysis is one of the tools those skilled in the art may employ to identify preferred embodiments of the compounds of the invention for use as therapeutic agents. Other methods of testing the compounds disclosed herein are also readily available to those skilled in the art. Thus, in addition, the determination of the ability of a compound to inhibit SCD may be accomplished in vivo. In one such embodiment this is accomplished by administering said chemical agent to an animal afflicted with a triglyceride (TG)- or very low density lipoprotein (VLDL)-related disorder and subsequently detecting a change in plasma triglyceride level in said animal thereby identifying a therapeutic agent useful in treating a triglyceride (-TG)- or very low density lipoprotein (VLDL)-related disorder. In such embodiment, the animal may be a human, such as a human patient afflicted with such a disorder and in need of treatment of said disorder.

In specific embodiments of such in vivo processes, said change in SCD1 activity in said animal is a decrease in activity, preferably wherein said SCD1 modulating agent does not substantially inhibit the biological activity of a delta-5 desaturase, delta-6 desaturase or fatty acid synthetase or other enzymes containing iron at the active site.

The model systems useful for compound evaluation may include, but are not limited to, the use of liver microsomes, such as from mice that have been maintained on a high carbohydrate diet, or from human donors, including persons suffering from obesity. Immortalized cell lines, such as HepG2 (from human liver), MCF-7 (from human breast cancer) and 3T3-L1 (from mouse adipocytes) may also be used. Primary cell lines, such as mouse primary hepatocytes, are also useful in testing the compounds of the invention. Where whole animals are used, mice used as a source of primary hepatocyte cells may also be used wherein the mice have been maintained on a high carbohydrate diet to increase SCD activity in mirocrosomes and/or to elevate plasma triglyceride levels (i.e., the 18:1/18:0 ratio); alternatively mice on a normal diet or mice with normal triglyceride levels may be used. Mouse models employing transgenic mice designed for hypertriglyceridemia are also available. Rabbits and hamsters are also useful as animal models, especially those expressing CETP (cholesterol ester transfer protein).

Another suitable method for determining the in vivo efficacy of the compounds of the invention is to indirectly measure their impact on inhibition of SCD enzyme by measuring a subject's Desaturation Index after administration of the compound.

"Desaturation Index" as employed in this specification means the ratio of the product over the substrate for the SCD enzyme as measured from a given tissue sample. This may be calculated using three different equations 18:1n-9/18:0 (oleic acid over stearic acid); 16:1n-7/16:0 (palmitoleic acid over palmitic acid); and/or 16:1n-7+18:1n-7/16:0 (measuring all reaction products of 16:0 desaturation over 16:0 substrate).

Desaturation Index is primarily measured in liver or plasma triglycerides, but may also be measured in other selected lipid fractions from a variety of tissues. Desaturation Index, generally speaking, is a tool for plasma lipid profiling.

A number of human diseases and disorders are the result of aberrant SCD1 biological activity and may be ameliorated by modulation of SCD1 biological activity using the therapeutic agents of the invention.

Inhibition of SCD expression may also affect the fatty acid composition of membrane phospholipids, as well as production or levels of triglycerides and cholesterol esters. The fatty acid composition of phospholipids ultimately determines membrane fluidity, with a subsequent modulation of the activity of multiple enzymes present within the membrane, while the effects on the composition of triglycerides and cholesterol esters can affect lipoprotein metabolism and adiposity.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented.

For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

Alternatively, another format can be used to measure the effect of SCD inhibition on sebaceous gland function. In a typical study using ridnets, oral, intravenous or topical formulations of the SCD inhibitor are administered to a rodent for a period of 1 to 8 days. Skin samples are taken and prepared for histological assessment to determine sebaceous gland number, size, or lipid content. A reduction of sebaceous gland size, number or function would indicate that the SCD inhibitor would have a beneficial impact on acne vulgaris, (Clark, S. B. et al. "Pharmacological modulation of sebaceous gland activity: mechanisms and clinical applications", *Dermatol. Clin.* (2007) Vol. 25, No. 2, pp 137-46. Geiger, J. M., "Retinoids and sebaceous gland activity" *Dermatology* (1995), Vol. 191, No. 4, pp 305-10).

Pharmaceutical Compositions of the Invention and Administration

The present invention also relates to pharmaceutical composition containing the compounds of the invention disclosed herein. In one embodiment, the present invention relates to a composition comprising compounds of the invention in a pharmaceutically acceptable carrier and in an amount effective to modulate triglyceride level or to treat diseases related to dyslipidemia and disorders of lipid metabolism, when administered to an animal, preferably a mammal, most preferably a human patient. In an embodiment of such composition, the patient has an elevated lipid level, such as elevated triglycerides or cholesterol, before administration of said compound of the invention and the compound of the invention is present in an amount effective to reduce said lipid level.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids, such as water, saline, glycerol and ethanol, and the like. A thorough discussion of pharmaceutically acceptable carriers, diluents, and other excipients is presented in REMINGTON'S PHARMACEUTICAL SCIENCES (Mack Pub. Co., N.J. current edition).

Those skilled in the art are familiar with how to determine suitable doses of the compounds for use in treating the diseases and disorders contemplated herein.

Therapeutic doses are generally identified through a dose ranging study in humans based on preliminary evidence derived from animal studies. Doses must be sufficient to result in a desired therapeutic benefit without causing unwanted side effects for the patient. The preferred dosage range for an animal is 0.001 mg/Kg to 10,000 mg/Kg, including 0.5 mg/Kg, 1.0 mg/Kg, 2.0 mg/Kg 5.0 mg/Kg and 10 mg/Kg, though doses outside this range may be acceptable. The dosing schedule may be once or twice per day, although more often or less often may be satisfactory.

Those skilled in the art are also familiar with determining administration methods (oral, intravenous, inhalation, subcutaneous, transdermal (topical), etc.), dosage forms, suitable pharmaceutical excipients and other matters relevant to the delivery of the compounds to a subject in need thereof.

In an alternative use of the invention, the compounds of the invention can be used in in vitro or in vivo studies as exemplary agents for comparative purposes to find other compounds also useful in treatment of, or protection from, the various diseases disclosed herein.

The pharmaceutical compositions according to the invention are those suitable for enteral, such as oral or rectal, transdermal and parenteral administration to mammals, including man, to inhibit stearoyl-CoA desaturase, and for the treatment of conditions associated with stearoyl desaturase activity. In general, the pharmaceutical compositions comprise a therapeutically effective amount of a pharmacologically active compound of the instant invention, alone or in combination with one or more pharmaceutically acceptable carriers.

The pharmacologically active compounds of the invention are useful in the manufacture of pharmaceutical compositions comprising a therapeutically effective amount thereof in conjunction or admixture with excipients or carriers suitable for either enteral or parenteral application. For enteral or parenteral application, it is preferred to administer an effective amount of a pharmaceutical composition according to the invention as tablets or gelatin capsules. Such pharmaceutical compositions may comprise, for example, the active ingredient together with diluents (e.g., lactose, dextrose, sucrose, mannitol, sorbitol, cellulose and/or glycine), lubricants (e.g., silica, talcum, stearic acid, its magnesium or calcium salt and/or polyethyleneglycol), and for tablets also comprises binders (e.g., magnesium aluminum silicate, starch paste, gelatin, tragacanth, methylcellulose, sodium carboxymethylcellulose and/or polyvinylpyrrolidone) and disintegrants (e.g., starches, agar, alginic acid or its sodium salt) or effervescent mixtures and absorbants, colorants, flavors and sweeteners.

In another aspect of the present invention the compounds may be in the form of injectable compositions, e.g. preferably aqueous isotonic solutions or suspensions, and suppositories, which can be advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions may be prepared according to conventional mixing, granulating or coating methods, and contain about 0.1-75%, preferably about 1-50%, of the active ingredient.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate-controlling barrier to deliver the compound of the skin of the host at a controlled and pre-determined rate over a prolonged period of time, and means to secure the device to the skin.

The most suitable route will depend on the nature and severity of the condition being treated. Those skilled in the art are also familiar with determining administration methods, dosage forms, suitable pharmaceutical excipients and other matters relevant to the delivery of the compounds to a subject in need thereof.

The compounds of the invention may be usefully combined with one or more other therapeutic agents for the treatment of SCD-mediated diseases and conditions. Preferably, the other therapeutic agent is selected from antidiabetics, hypolipidemic agents, anti-obesity agents, anti-hypertensive agents or inotropic agents.

Thus, an additional aspect of the present invention concerns a pharmaceutical composition comprising a therapeutically effective amount of a compound of the invention in combination with one or more other therapeutic agents. For example, the composition can be formulated to comprise a therapeutically effective amount of a compound of the invention as defined above, in combination with another therapeutic agent, each at an effective therapeutic dose as reported in the art. Such therapeutic agents may, for example, include insulin, insulin derivatives and mimetics; insulin secretagogues, such as the sulfonylureas, e.g., Glipizide, glyburide and Amaryl; insulinotropic sulfonylurea receptor ligands, such as meglitinides, e.g., nateglinide and repaglinide; PPARγ and/or PPARα (peroxisome proliferator-activated receptor) ligands such as MCC-555, MK767, L-165041, GW7282 or thiazolidinediones such as rosiglitazone, pioglitazone, troglitazone; insulin sensitizers, such as protein tyrosine phosphatase-1B (PTP-1B) inhibitors such as PTP-112; GSK3 (glycogen synthase kinase-3) inhibitors such as SB-517955, SB-4195052, SB-216763, NN-57-05441, NN-57-05445 or RXR ligands such as GW-0791, AGN-194204; sodium-dependent glucose cotransporter inhibitors, such as T-1095, glycogen phosphorylase A inhibitors, such as BAY R3401; biguanides, such as metformin; alpha-glucosidase inhibitors, such as acarbose; GLP-1 (glucagon like peptide-1), GLP-1 analogs, such as Exendin-4, and GLP-1 mimetics; DPPIV (dipeptidyl peptidase IV) inhibitors such as LAF237 (Vildagliptin); hypolipidemic agents, such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin, fluindostatin and rivastatin, squalene synthase inhibitors or FXR (farnesoid X receptor) and LXR (liver X receptor) ligands, cholestyramine, fibrates, nicotinic acid and aspirin; anti-obesity agents, such as orlistat, anti-hypertensive agents, inotropic agents and hypolipidemic agents, e.g., loop diuretics, such as ethacrynic acid, furosemide and torsemide; angiotensin converting enzyme (ACE) inhibitors, such as benazepril, captopril, enalapril, fosinopril, lisinopril, moexipril, perinodopril, quinapril, ramipril and trandolapril; inhibitors of the Na-K-ATPase membrane pump, such as digoxin; neutralendopeptidase (NEP) inhibitors; ACE/NEP inhibitors, such as omapatrilat, sampatrilat and fasidotril; angiotensin II antagonists, such as candesartan, eprosartan, irbesartan, losartan, telmisartan and valsartan, in particular valsartan; β-adrenergic receptor blockers, such as acebutolol, atenolol, betaxolol, bisoprolol, metoprolol, nadolol, propranolol, sotalol and timolol; inotropic agents, such as digoxin, dobutamine and milrinone; calcium channel blockers, such as amlodipine, bepridil, diltiazem, felodipine, nicardipine, nimodipine, nifedipine, nisoldipine and verapamil. Other specific antidiabetic compounds are described by Patel Mona (*Expert Opin Investig Drugs*. (2003) April; 12(4):623-33) in the FIGS. 1 to 7, which are herein incorporated by reference. A compound of the present invention may be administered either simultaneously, before or after the other active ingredient, either separately by the same or different route of administration or together in the same pharmaceutical formulation.

The structure of the active agents identified by code numbers (nos.), generic or trade names may be taken from the actual edition of the standard compendium "The Merck Index" or from databases, e.g. Patents International (e.g. IMS World Publications). The corresponding content thereof is hereby incorporated by reference.

In another aspect is the use of the pharmaceutical composition as described above for production of a medicament for the treatment of SCD-mediated disease or conditions.

In another aspect is the use of a pharmaceutical composition or combination as described above for the preparation of a medicament for the treatment of conditions associated with stearoyl-CoA desatruase activity.

A pharmaceutical composition as described above for the treatment of conditions associated with the inhibition of stearoyl-CoA desaturase.

Preparations of Compounds

It is understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters.

Protecting groups may be added or removed in accordance with standard techniques, which are well-known to those skilled in the art and as described herein.

The use of protecting groups is described in detail in Green, T. W. and P. G. M. Wuts, *Greene's Protective Groups in Organic Synthesis* (2006), 4th Ed., Wiley. The protecting group may also be a polymer resin such as a Wang resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

The following reaction schemes illustrate methods to make compounds of this invention. It is understood that one skilled in the art would be able to make these compounds by similar methods or by methods known to one skilled in the art. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Advanced Organic Chemistry: Reactions, Mechanisms, and Structure, 5th edition (Wiley, December 2000)) or prepared as described in this invention. $R^1$, $R^2$, $R^3$, $R^4$, $R^5$, X, Y, W and V are defined as in the Specification unless specifically defined. R' is a protecting group.

In general, the compounds of Formula (I) of this invention can be synthesized following the general procedure as described in Reaction Scheme 1, where W is —N($R^5$)C(O)—.

Reaction Scheme 1

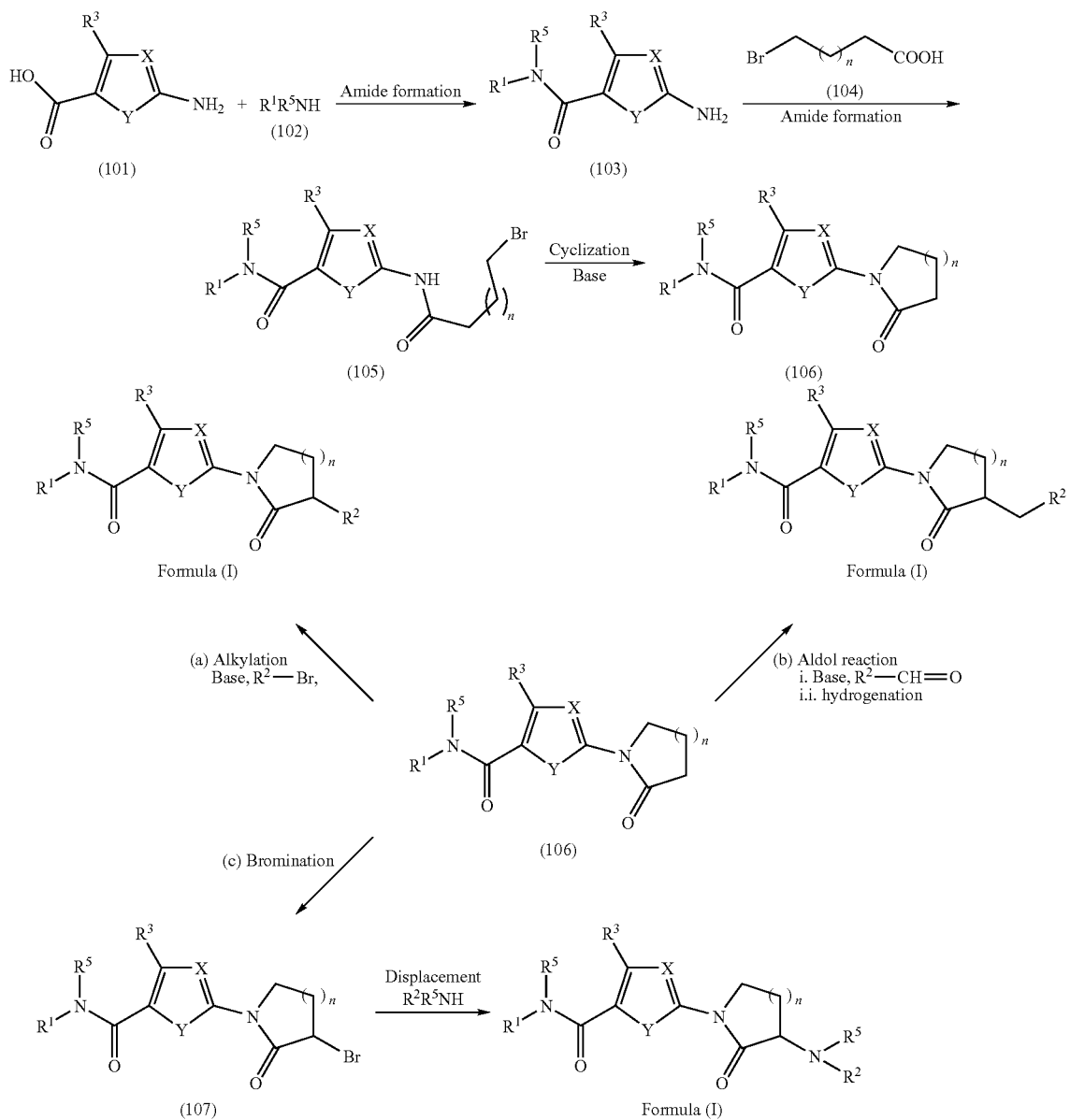

The starting materials for the above reaction scheme are commercially available or can be prepared according to methods known to one skilled in the art or by methods disclosed herein. In general, the compounds of the invention are prepared in the above reaction scheme as follows:

The coupling of the amino carboxylic acid (101) and amine compound (102) under standard amide bond formation conditions known to the one skilled in the art affords compound (103). Compound (103) undergoes another amide bond formation reaction with acid (104) to generate compound (105) which undergoes intramolecular cyclization in the presence of a base, such as, but not limited to, potassium carbonate to afford the cyclized compound (106). Compound (106) is used as a key intermediate to generate compounds of Formula (I) under the conditions of (a) alkylation, or (b) aldol condensation followed by hydrogenation, or (c) bromination to generate compound (107), followed by amine displacement.

Alternatively, the compounds of Formula (I) of this invention can be synthesized following the general procedure as described in Reaction Scheme 2, where W is —N($R^5$)C (O)—.

Reaction Scheme 2

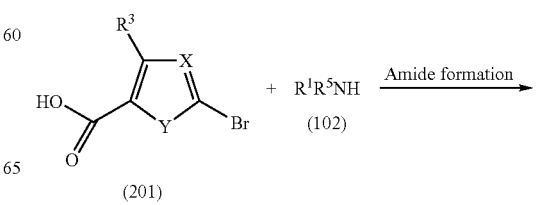

-continued

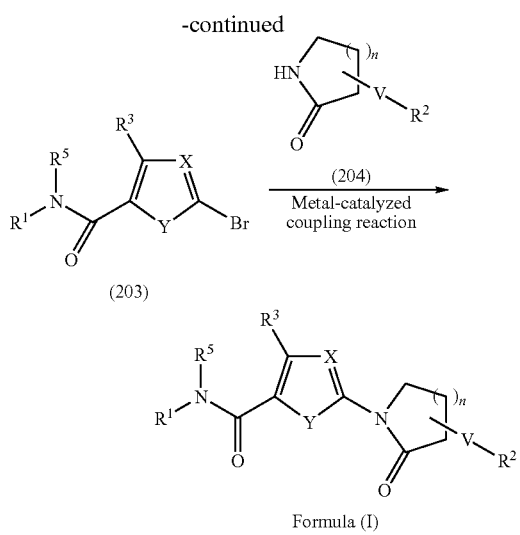

Formula (I)

The starting materials for the above reaction scheme are commercially available or can be prepared according to methods known to one skilled in the art or by methods disclosed herein. In general, the compounds of the invention are prepared in the above reaction scheme as follows:

The starting compound (201) undergoes coupling reaction with amine (102) under standard amide bond formation conditions known to the one skilled in the art to afford compound (203). Compound (203) is then coupled with compound (204) under metal catalyzed reaction conditions to generate compound of Formula (I), where W is —N($R^5$)C(O)—.

Alternatively, the compounds of Formula (I) of this invention can be synthesized following the general procedure as described in Reaction Scheme 3 where W is —N($R^5$)C(O)—.

Reaction Scheme 3

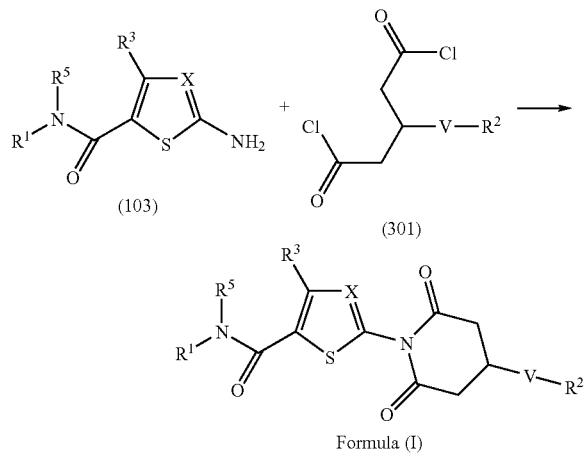

Formula (I)

The starting materials for the above reaction scheme are commercially available or can be prepared according to methods known to one skilled in the art or by methods disclosed herein. In general, the compounds of the invention are prepared in the above reaction scheme as follows:

The starting amino compound (103) reacts with compound (301) in the presence of a base, such as, but not limited to, triethylamine, to afford compound of Formula (I).

Although one skilled in the art is capable of preparing the compounds of the invention according to the general techniques disclosed above, more specific details on synthetic techniques for compounds of the invention are provided elsewhere in this specification for convenience. Again, all reagents and reaction conditions employed in synthesis are known to those skilled in the art and are available from ordinary commercial sources.

Preparation 1

Preparation of 2-amino-N-benzyl-4-methylthiazole-5-carboxamide

A. A mixture of ethyl 2-amino-4-methylthiazole-5-carboxylate (6.58 g, 35.5 mmol) and NaOH (5.40 g, 135.0 mmol) in tetrahydrofuran (60 mL) and water (30 mL) was heated to reflux overnight. Tetrahydrofuran was removed in vacuo, and the residue was neutralized with 5% hydrochloric acid solution to pH 56. The precipitate obtained was collected by filtration and dried to afford the crude 2-amino-4-methylthiazole-5-carboxylic acid (5.20 g, 94%): $^1$H NMR (300 MHz, DMSO-$d_6$) δ 7.63 (s, 2H), 2.30 (s, 3H); MS (ES+) m/z 159.1 (M+1).

B. To a suspension of 2-amino-4-methylthiazole-5-carboxylic acid (5.20 g, 32.9 mmol) and N,N-diisopropylethylamine (15 mL, 86.7 mmol) in N,N-dimethylformamide (40 mL) was added N-(3-dimethylaminopropyl)-N'-ethylcarbodiimide hydrochloride (8.18 g, 42.7 mmol). The resulting mixture was stirred for 30 min, then 1-hydroxybenzotriazole hydrate (5.78 g, 42.7 mmol) was added, followed by the addition of benzylamine (4.3 mL, 39.3 mmol). The reaction mixture was stirred at ambient temperature for 2 days, then diluted with ethyl acetate, washed with water and brine, dried over anhydrous sodium sulfate and filtered. The filtrate was concentrated in vacuo. The residue was purified by column chromatography to afford the title compound in 60% yield (4.90 g): $^1$H NMR (300 MHz, DMSO-$d_6$) δ 7.36-7.25 (m, 5H), 5.79 (br s, 1H), 5.36 (br s, 2H), 4.54 (d, J=5.7 Hz, 2H), 2.47 (s, 3H); MS (ES+) m/z 248.4 (M+1).

Preparation 2

Preparation of 2-amino-N-(4-fluorobenzyl)-4-methylthiazole-5-carboxamide

To a solution of 2-amino-4-methylthiazole-5-carboxylic acid (4.20 g, 26.0 mmol) in anhydrous N,N-dimethylformamide (100 mL) was added 1-hydroxybenzotriazole (9.30 g, 69.0 mmol), N-(3-dimethylaminopropyl)-N'-ethylcarbodiimide (6.60 g, 34.0 mmol), diisopropylethylamine (4.40 g, 34.0 mmol), and (4-fluorophenyl)methanamine (3.97 g, 32.0 mmol). The reaction mixture was stirred at ambient temperature for 18 hours and N,N-dimethylformamide was removed in vacuo. The residue was dissolved in ethyl acetate (400 mL) and washed with saturated aqueous sodium bicarbonate (2×100 mL) and brine (100 mL). The organic layer was dried over anhydrous sodium sulfate, filtered and the filtrate was concentrated in vacuo to afford the title compound as a yellowish solid in 80% yield (5.60 g): $^1$H NMR (300 MHz, CDCl$_3$) δ 7.39-7.17 (m, 2H), 7.01 (t, J=8.3 Hz, 2H), 5.78 (br s, 1H), 5.34 (br s, 2H), 4.50 (d, J=5.6 Hz, 2H), 2.47 (s, 3H); MS (ES+) m/z 266.2 (M+1).

Preparation 3

Preparation of N-benzyl-2-(4-bromobutanamido)-4-methylthiazole-5-carboxamide

To a solution of 4-bromobutyric acid (0.94 g, 5.50 mmol) and 4-methylmorpholine (0.70 mL, 6.20 mmol) in tetrahydrofuran (40 mL) was added isobutyl chloroformate (0.75 mL, 5.60 mmol) at 0° C. The resulting reaction mixture was stirred at 0° C. for 2 hours and then 2-amino-N-benzyl-4-methylthiazole-5-carboxamide (1.24 g, 5.00 mmol) was added. After 14 hours at ambient temperature, the solvent was removed in vacuo, and the residue was dissolved in ethyl acetate (200 mL), washed with water and brine, dried over anhydrous sodium sulfate and filtered. The filtrate was concentrated and the residue was purified by column chromatography to yield the title compound (1.80 g, 90%): $^1$H NMR (300 MHz, CDCl$_3$) δ 7.30-7.23 (m, 5H), 5.99 (s, 1H), 4.57-4.55 (m, 2H), 4.34-4.27 (m, 2H), 3.38-3.44 (m, 2H), 2.64-2.18 (m, 5H); MS (ES+) m/z 396.3 (M+1) and 398.3 (M+1).

Preparation 4

Preparation of 2-(4-bromobutanamido)-N-(4-fluorobenzyl)-4-methylthiazole-5-carboxamide To a solution of 4-bromobutanoic acid (4.40 g, 26.0 mmol) in anhydrous dichloromethane (100 mL) was added two drops of N,N'-dimethylformamide, followed by the addition of oxalyl chloride (4.99 g, 39.0 mmol) dropwise. The reaction was stirred at ambient temperature for 4 hours. The solvent was removed in vacuo to afford 4-bromobutanoyl chloride (4.87 g, 26.0 mmol) as a yellow oil, which was used in the next step without further purification.

To a solution of 2-amino-N-(4-fluorobenzyl)-4-methylthiazole-5-carboxamide (5.60 g, 22.0 mmol) and triethylamine (2.61 g, 26.0 mmol) in anhydrous tetrahydrofuran (250 mL) was added 4-bromobutanoyl chloride (4.99 g, 26.0 mmol) in anhydrous dichloromethane (10 mL) dropwise at 0° C. The reaction mixture was stirred at ambient temperature for 2 hours, then diluted with dichloromethane (200 mL) and washed with saturated aqueous sodium bicarbonate solution (2×150 mL), and brine (150 mL). The organic layer was dried over anhydrous sodium sulfate, filtered and the filtrate was concentrate in vacuo to afford the title compound as a yellow oil in 92% yield (8.00 g): $^1$H NMR (300 MHz, CDCl$_3$) δ 8.61 (br s, 1H), 7.32-7.22 (m, 2H), 7.05-6.94 (m, 2H), 6.14 (t, J=5.6 Hz, 1H), 4.53 (d, J=5.6 Hz, 2H), 3.45 (t, J=6.7 Hz, 2H), 2.65 (t, J=6.7 Hz, 2H), 2.58 (s, 3H), 2.23 (quintet, J=6.7 Hz, 2H); MS (ES+) m/z 413.1 (M+1), 415.1 (M+1).

Preparation 5

Preparation of 3-(4-fluorobenzyl)pyrrolidin-2-one

A. To a solution of pyrrolidin-2-one (1.00 g, 12.0 mmol) in anhydrous toluene (20 mL) was added trifluoroacetic anhydride (2.30 mL, 16.0 mmol) dropwise at 0° C. The reaction mixture was stirred at ambient temperature for 1 hour and concentrated in vacuo. The residue was evaporated in vacuo with anhydrous toluene (3×20 mL) to afford 1-(2,2,2-trifluoroacetyl)pyrrolidin-2-one as a clear oil (2.12 g, 99%): $^1$H NMR (300 MHz, CDCl$_3$) δ 3.85 (t, J=7.2 Hz, 2H), 2.61 (t, J=8.1 Hz, 2H), 2.22-2.04 (m, 2H).

B. To a suspension of potassium tert-butoxide (2.00 g, 18.0 mmol) in anhydrous tetrahydrofuran (40 mL) was added a mixture of 1-(2,2,2-trifluoroacetyl)-pyrrolidin-2-one (2.12 g, 12.0 mmol) and 4-fluorobenzaldehyde (1.24 mL, 12.0 mmol) in anhydrous tetrahydrofuran (5 mL) dropwise at 0° C. The reaction mixture was stirred at ambient temperature for 2 hours, then refluxed for 1 hour and concentrated in vacuo. Water (150 mL) was added to the residue. The white solid precipitated was filtered and re-dissolved in ethyl acetate (50 mL) and then hydrogenated in the presence of catalytic amount of palladium on carbon (20% w/w) at ambient temperature and atmospheric pressure for 3 hours. The reaction mixture was filtered through a bed of celite. The filtrate was concentrated in vacuo and the residue was purified by column chromatography (ethyl acetate) to afford the title compound as a white solid (0.72 g, 35%): $^1$H NMR (300 MHz, CDCl$_3$) δ 7.20-7.09 (m, 2H), 7.00-6.90 (m, 2H), 6.42 (s, 1H), 3.31-3.07 (m, 3H), 2.71-2.54 (m, 2H), 2.19-2.03 (m, 1H), 1.89-1.69 (m, 1H); MS (ES+) m/z 194.1 (M+1).

Preparation 6

Preparation of 3-(4-(trifluoromethoxy)benzyl)pyrrolidin-2-one

Following the procedure as described in Preparation 5, making variations as required to use 4-(trifluoromethoxy) benzaldehyde in place of 4-fluorobenzaldehyde to react with 1-(2,2,2-trifluoroacetyl)pyrrolidin-2-one, the title compound was obtained as a white solid in 53% yield: $^1$H NMR (300 MHz, CDCl$_3$) δ 7.24-7.06 (m, 4H), 3.71-3.50 (m, 2H), 3.34-3.02 (m, 3H), 2.19-2.00 (m, 1H), 1.83-1.70 (m, 1H); MS (ES+) m/z 260.1 (M+1).

Preparation 7

Preparation of 2-bromo-4-methyl-N-(pyridin-3-ylmethyl)thiazole-5-carboxamide

To a solution of 2-bromo-4-methylthiazole-5-carboxylic acid (2.25 g, 10.0 mmol) and 4-methylmorpholine (1.25 g, 11.0 mmol) in anhydrous dichloromethane (80 mL) was added isobutylchloroformate (1.33 mL, 10.0 mmol) dropwise at 0° C. After stirring at ambient temperature for 2 hours, the reaction mixture was cooled to 0° C. and pyridin-3-ylmethanamine (1.23 g, 12.0 mmol) was added dropwise. The reaction mixture was stirred at ambient temperature for 4 hours, diluted with ethyl acetate (100 mL) and washed with saturated aqueous sodium bicarbonate (50 mL) and brine (50 mL). The organic layer was dried over anhydrous sodium sulfate, filtered and the filtrate was concentrated in vacuo. The residue was purified by column chromatography (ethyl acetate) to afford the title compound as a yellow solid (1.78 g, 56%): $^1$H NMR (300 MHz, CDCl$_3$) δ 8.51 (d, J=2.5 Hz, 2H), 7.67 (td, J=7.8, 1.9 Hz, 1H), 7.29-7.26 (m, 1H), 6.36 (br s, 1H), 4.56 (d, J=5.9 Hz, 2H), 2.63 (s, 3H); MS (ES+) m/z 312.1 (M+1), 314.1 (M+1).

Preparation 8

Preparation of N-benzyl-2-bromo-4-methylthiazole-5-carboxamide

Following the procedure as described in Preparation 7, making variations as required to use benzylamine in place of pyridin-3-ylmethanamine to react with 2-bromo-4-methylthiazole-5-carboxylic acid, the title compound was obtained as a yellow solid in 60% yield: $^1$H NMR (300 MHz, CDCl$_3$) δ 7.41-7.26 (m, 5H), 5.99 (br s, 1H), 4.56 (d, J=5.7 Hz, 2H), 2.63 (s, 3H); MS (ES+) m/z 311.2 (M+1), 313.2 (M+1).

Preparation 9

Preparation of N-benzyl-2-(5-bromopentanamido)-4-methylthiazole-5-carboxamide

To a mixture 2-amino-N-benzyl-4-methylthiazole-5-carboxamide (1.29 g, 5.20 mmol) and triethylamine (0.58 g, 5.72 mmol) in anhydrous dichloromethane (25.0 mL) was added dropwise 5-bromopentanoyl chloride (1.141 g, 5.72 mmol) in anhydrous dichloromethane (10 mL) at 0° C. The reaction mixture was stirred at ambient temperature for 2 hours, then diluted with dichloromethane (40 mL) and washed with saturated aqueous sodium bicarbonate solution (2×50 mL) and brine (50 mL). The organic phase was dried over anhydrous sodium sulfate, filtered, and the filtrate was concentrate in vacuo to afford the title compound as a yellow oil (1.91 g, 92%): $^1$H NMR (300 MHz, CDCl$_3$) δ 8.81 (br s, 1H), 7.33-7.23 (m, 5H), 5.91 (s, 1H), 4.14 (d, J=5.6 Hz, 2H), 3.51 (t, J=6.7 Hz, 2H), 2.46 (s, 3H), 2.35 (t, J=6.7 Hz, 2H), 1.82 (m, 2H), 1.53 (m, 2H); MS (ES+) m/z 410.1 (M+1), 412.1 (M+1).

Example 1

Synthesis of N-benzyl-4-methyl-2-(2-oxopyrrolidin-1-yl)thiazole-5-carboxamide

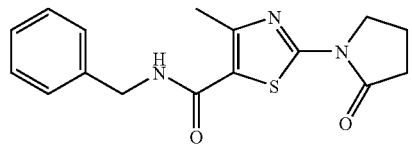

To a solution of N-benzyl-2-(4-bromobutanamido)-4-methylthiazole-5-carboxamide (1.80 g, 4.54 mmol) in acetone (50 mL) and water (5 mL) was added potassium carbonate (1.50 g, 10.8 mmol) at ambient temperature. The resulting reaction mixture was stirred at ambient temperature for 2 hours. The solvent was removed in vacuo, and the residue was washed with water and t-butyl methyl ether to yield the title compound in 78% yield (1.12 g): mp 222-224° C.; $^1$H NMR (300 MHz, DMSO-d$_6$) δ 8.60 (t, J=6.0 Hz, 1H), 7.33-7.16 (m, 5H), 4.35 (d, J=6.0 Hz, 2H), 3.97 (t, J=7.2 Hz, 2H), 2.59 (t, J=7.8 Hz, 2H), 2.46 (s, 3H), 2.14-1.94 (m, 2H); MS (ES+) m/z 316.4 (M+1).

Example 1.1

Synthesis of N-(4-fluorobenzyl)-4-methyl-2-(2-oxopyrrolidin-1-yl)thiazole-5-carboxamide

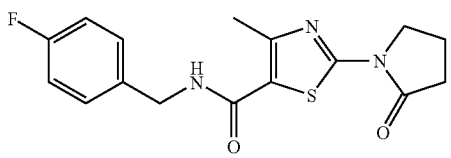

Following the procedure as described in Example 1, making variations as required to use 2-(4-bromobutanamido)-N-(4-fluorobenzyl)-4-methylthiazole-5-carboxamide in replace of N-benzyl-2-(4-bromobutanamido)-4-methylthiazole-5-carboxamide, the title compound was obtained as a white solid in 85% yield: $^1$H NMR (300 MHz, CD$_3$OD) δ 7.39-7.33 (m, 2H), 7.09-7.02 (m, 2H), 4.48 (s, 2H), 4.15-4.09 (m, 2H), 2.68 (t, J=8.1 Hz, 2H), 2.55 (s, 3H), 2.25 (m, 2H); MS (ES+) m/z 334.2 (M+1).

Example 1.2

Synthesis of N-benzyl-4-methyl-2-(2-oxopiperidin-1-yl)thiazole-5-carboxamide

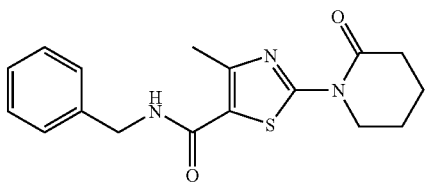

Following the procedure as described in Example 1, making variations as required to use N-benzyl-2-(5-bromopentanamido)-4-methylthiazole-5-carboxamide in replace of N-benzyl-2-(4-bromobutanamido)-4-methylthiazole-5-carboxamide, the title compound was obtained as a white solid in 35% yield: mp 175-176° C.; $^1$H NMR (300 MHz, DMSO-d$_6$) δ 7.33-7.25 (m, 5H), 5.96 (s, 1H), 4.57 (d, J=5.6 Hz, 2H), 4.13 (t, J=6.0 Hz, 2H), 2.66 (t, J=6.8 Hz, 2H), 2.64 (s, 3H), 2.02-1.87 (m, 4H); $^{13}$C NMR (75 MHz, CDCl$_3$) δ 169.8, 162.7, 156.9, 152.0, 138.0, 128.8, 127.9, 127.6, 119.4, 48.0, 44.0, 32.7, 22.5, 20.2, 17.4; MS (ES+) m/z 330.6 (M+1).

Example 1.3

Synthesis of N-(3-fluorobenzyl)-4-methyl-2-(2-oxopiperidin-1-yl)thiazole-5-carboxamide

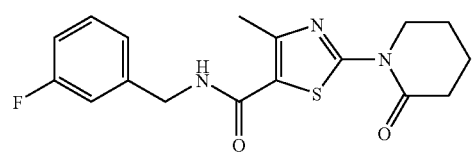

Following the procedure as described in Example 1, making variations as required to use 2-(5-bromopentanamido)-N-(3-fluorobenzyl)-4-methylthiazole-5-carboxamide in place of N-benzyl-2-(4-bromobutanamido)-4-methylthiazole-5-carboxamide, the title compound was obtained as a white solid in 85% yield: $^1$H NMR (300 MHz, CDCl$_3$) δ 7.35-7.23 (m, 1H), 7.15-6.91 (m, 3H), 6.08 (t, J=5.6 Hz, 1H), 4.55 (d, J=5.6 Hz, 2H), 4.12 (t, J=6.0 Hz, 2H), 2.70-2.61 (m, 5H), 2.05-1.84 (m, 4H).

Example 2

Synthesis of N-(4-fluorobenzyl)-4-methyl-2-(2-oxo-3-(4-(trifluoromethyl)benzyl)pyrrolidin-1-yl)thiazole-5-carboxamide

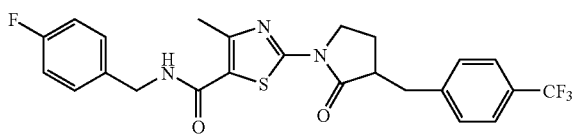

To a solution of N-(4-fluorobenzyl)-4-methyl-2-(2-oxopyrrolidin-1-yl)thiazole-5-carboxamide (0.13 g, 0.38 mmol) in a mixture of anhydrous tetrahydrofuran and 1,3-dimethyl-3,4,5,6-tetrahydro-2(1H)-pyrimidinone (8/1, v/v) at −78° C. was added lithium bis(trimethylsilyl)amide in tetrahydrofuran (0.83 mL, 0.83 mmol) dropwise. The reaction mixture was stirred at −78° C. for 5 minutes, followed by the addition of 1-(bromomethyl)-4-(trifluoromethyl)benzene (0.058 mL, 0.38 mmol) dropwise. The reaction mixture was warmed to −30° C. in 30 minutes. Aqueous saturated ammonium chloride solution (10 mL) was added, followed by extraction with dichloromethane (3×10 mL). The combined organic solutions were dried over anhydrous sodium sulfate, filtered and concentrated in vacuo. The residue was purified by column chromatography (ethyl acetate/hexanes (1/1)) to afford the title compound as a white solid (0.075 g, 41%): mp 175-176° C. (hexanes/ethyl acetate); $^1$H NMR (300 MHz, CDCl$_3$) δ 7.53 (d, J=7.9 Hz, 2H), 7.32-7.24 (m, 4H), 7.01 (t, J=8.9 Hz, 2H), 6.03 (t, J=5.6 Hz, 1H), 4.52 (d, J=5.6 Hz, 2H), 4.17-4.04 (m, 1H), 3.91-3.81 (m, 1H), 3.30 (dd, J=13.8, 4.3 Hz, 1H), 3.06-2.99 (m, 1H), 2.85 (dd, J=13.8, 8.9 Hz, 1H), 2.61 (s, 3H), 2.32-2.21 (m, 1H), 1.93-1.83 (m, 1H); $^{13}$C NMR (75 MHz, CDCl$_3$) δ 174.4, 162.3, 155.3, 152.8, 142.4, 133.8, 129.9, 129.6, 129.3, 125.6, 118.6, 115.7, 115.6, 45.9, 44.2, 43.4, 36.2, 24.4, 17.3; MS (ES+) m/z 492.3 (M+1).

Example 2.1

Synthesis of N-(4-fluorobenzyl)-2-(3-(4-fluorobenzyl)-2-oxopyrrolidin-1-yl)-4-methylthiazole-5-carboxamide

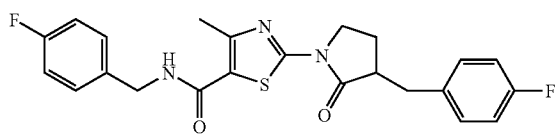

Following the procedure as described in Example 2, making variation as required to use 1-(bromomethyl)-4-fluorobenzene in place of 1-(bromomethyl)-4-(trifluoromethyl)benzene to react with N-(4-fluorobenzyl)-4-methyl-2-(2-oxopyrrolidin-1-yl)thiazole-5-carboxamide, the title compound was obtained as a white solid in 36% yield: mp 196-197° C. (hexanes/ethyl acetate); $^1$H NMR (300 MHz, CDCl$_3$) δ 7.31-7.26 (m, 2H), 7.13 (dd, J=8.6, 5.6 Hz, 2H), 7.06-6.90 (m, 4H), 6.03 (t, J=5.6 Hz, 1H), 4.52 (d, J=5.6 Hz, 2H), 4.06-3.95 (m, 1H), 3.95-3.70 (m, 1H), 3.29-3.10 (m, 1H), 3.05-2.92 (m, 1H), 2.88-2.70 (m, 1H), 2.60 (s, 3H), 2.32-2.17 (m, 1H), 2.00-1.80 (m, 1H); $^{13}$C NMR (75 MHz, CDCl$_3$) δ 174.8, 176.3, 162.3, 161.8, 155.4, 152.9, 133.8, 133.7, 130.4, 129.6, 118.5, 115.7, 115.5, 45.9, 44.4, 43.4, 35.6, 24.2, 17.3; MS (ES+) m/z 442.2 (M+1).

Example 2.2

Synthesis of 2-(3-(4-(difluoromethoxy)benzyl)-2-oxopyrrolidin-1-yl)-N-(4-fluorobenzyl)-4-methylthiazole-5-carboxamide

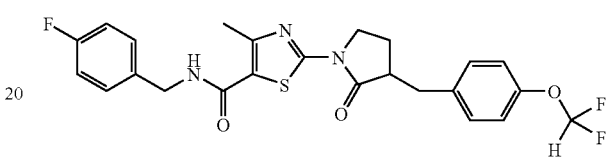

Following the procedure as described in Example 2, making variation as required to use 1-(bromomethyl)-4-(difluoromethoxy)benzene in place of 1-(bromomethyl)-4-(trifluoromethyl)benzene to react with N-(4-fluorobenzyl)-4-methyl-2-(2-oxopyrrolidin-1-yl)thiazole-5-carboxamide, the title compound was obtained as a white solid in 31% yield: mp 143-145° C. (hexanes/ethyl acetate); $^1$H NMR (300 MHz, CDCl$_3$) δ 7.34-7.22 (m, 2H), 7.16 (d, J=8.4 Hz, 2H), 7.06-6.93 (m, 4H), 6.45 (t, J=73.9 Hz, 1H), 6.08 (t, J=5.6 Hz, 1H), 4.51 (d, J=5.6 Hz, 2H), 4.09-3.99 (m, 1H), 3.91-3.78 (m, 1H), 3.25-3.12 (m, 1H), 3.05-2.94 (m, 1H), 2.83-2.73 (m, 1H), 2.59 (s, 3H), 2.32-2.18 (m, 1H), 1.98-1.81 (m, 1H); $^{13}$C NMR (75 MHz, CDCl$_3$) δ 174.7, 162.3, 162.2, 160.6, 155.4, 152.7, 149.9, 135.4, 133.8, 130.3, 129.6, 119.8, 115.6, 112.4, 45.9, 44.3, 43.3, 35.6, 24.2, 17.2; MS (ES+) m/z 490.3 (M+1).

Example 2.3

Synthesis of N-(4-fluorobenzyl)-4-methyl-2-(2-oxo-3-(4-(trifluoromethoxy)benzyl)pyrrolidin-1-yl)thiazole-5-carboxamide

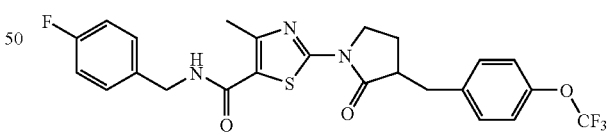

Following the procedure as described in Example 2, making variation as required to use 1-(bromomethyl)-4-(trifluoromethoxy)benzene in place of 1-(bromomethyl)-4-(trifluoromethyl)benzene to react with N-(4-fluorobenzyl)-4-methyl-2-(2-oxopyrrolidin-1-yl)thiazole-5-carboxamide, the title compound was obtained as a white solid in 26% yield: mp 165-166° C. (hexanes/ethyl acetate); $^1$H NMR (300 MHz, CDCl$_3$) δ 7.34-7.16 (m, 4H), 7.12 (d, J=8.6 Hz, 2H), 7.01 (t, J=8.6 Hz, 2H), 6.02 (t, J=5.6 Hz, 1H), 4.52 (d, J=5.6 Hz, 2H), 4.09-4.02 (m, 1H), 3.93-3.79 (m, 1H), 3.29-3.20 (m, 1H), 3.05-2.95 (m, 1H), 2.85-2.75 (m, 1H), 2.60 (s, 3H), 2.35-2.19 (m, 1H), 1.99-1.81 (m, 1H); $^{13}$C NMR (75 MHz, CDCl$_3$) δ

174.6, 162.3, 155.4, 152.8, 148.1, 136.9, 133.7, 131.6, 130.3, 129.6, 121.2, 118.6, 115.7, 45.9, 44.3, 43.4, 35.7, 24.3, 17.2; MS (ES+) m/z 508.3 (M+1).

Example 2.4

Synthesis of N-benzyl-4-methyl-2-(2-oxo-3-(4-(trifluoromethyl)benzyl)pyrrolidin-1-yl)thiazole-5-carboxamide

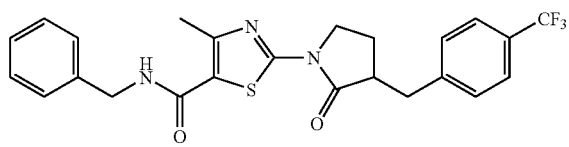

Following the procedure as described in Example 2, making variation as required to use N-benzyl-4-methyl-2-(2-oxopyrrolidin-1-yl)thiazole-5-carboxamide in place of N-(4-fluorobenzyl)-4-methyl-2-(2-oxopyrrolidin-1-yl)thiazole-5-carboxamide to react with 1-(bromomethyl)-4-(trifluoromethyl)benzene, the title compound was obtained as a white solid in 27% yield: mp 174-175° C. (hexanes/ethyl acetate); $^1$H NMR (300 MHz, CDCl$_3$) δ 7.54 (d, J=8.0 Hz, 2H), 7.39-7.20 (m, 7H), 6.01 (t, J=5.6 Hz, 1H), 4.57 (d, J=5.6 Hz, 2H), 4.14-4.02 (m, 1H), 3.93-3.79 (m, 1H), 3.35-3.24 (m, 1H), 3.09-2.96 (m 1H), 2.90-2.80 (m, 1H), 2.61 (s, 3H), 2.34-2.19 (m, 1H), 1.95-1.81 (m, 1H); $^{13}$C NMR (75 MHz, CDCl$_3$) δ 174.4, 162.3, 155.3, 152.6, 142.4, 137.8, 129.3, 128.8, 127.9, 127.7, 125.7, 125.6, 125.5, 118.8, 45.9, 44.2, 44.1, 36.2, 24.4, 17.2; MS (ES+) m/z 474.1 (M+1).

Example 2.5

Synthesis of N-benzyl-2-(3-(4-(difluoromethoxy)benzyl)-2-oxopyrrolidin-1-yl)-4-methylthiazole-5-carboxamide

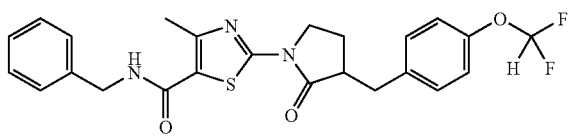

Following the procedure as described in Example 2, making variation as required to use N-benzyl-4-methyl-2-(2-oxopyrrolidin-1-yl)thiazole-5-carboxamide in place of N-(4-fluorobenzyl)-4-methyl-2-(2-oxopyrrolidin-1-yl)thiazole-5-carboxamide to react with 1-(bromomethyl)-4-(difluoromethoxy)benzene in place of 1-(bromomethyl)-4-(trifluoromethyl)benzene, the title compound was obtained as a white solid in 27% yield: mp 132-133° C. (hexanes/ethyl acetate); $^1$H NMR (300 MHz, CDCl$_3$) δ 7.41-7.24 (m, 5H), 7.18 (d, J=8.2 Hz, 2H), 7.03 (d, J=8.2 Hz, 2H), 6.46 (dt, J=73.9, 1.0 Hz, 1H), 5.94 (t, J=5.5 Hz, 1H), 4.57 (d, J=5.5 Hz, 2H), 4.11-3.98 (m, 1H), 3.93-3.81 (m, 1H), 3.28-3.16 (m, 1H), 3.08-2.93 (m, 1H), 2.80 (dd, J=13.7, 8.8 Hz, 1H), 2.62 (s, 3H), 2.33-2.19 (m, 1H), 1.99-1.84 (m, 1H); $^{13}$C NMR (75 MHz, CDCl$_3$) δ 174.6, 162.3, 155.3, 152.7, 137.8, 135.4, 130.3, 128.8, 127.9, 127.7, 119.9, 119.5, 118.7, 115.9, 45.9, 44.4, 44.1, 35.6, 24.2, 17.3; MS (ES+) m/z 472.3 (M+1).

Example 2.6

Synthesis of N-benzyl-4-methyl-2-(2-oxo-3-(4-(trifluoromethyl)benzyl)piperidin-1-yl)thiazole-5-carboxamide

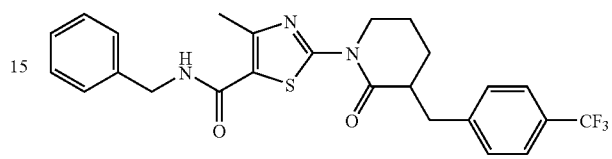

Following the procedure as described in Example 2, making variation as required to use N-benzyl-4-methyl-2-(2-oxopiperidin-1-yl)thiazole-5-carboxamide in place of N-(4-fluorobenzyl)-4-methyl-2-(2-oxopyrrolidin-1-yl)thiazole-5-carboxamide to react with 1-(bromomethyl)-4-(trifluoromethyl)benzene, the title compound was obtained as a white solid in 47% yield: mp 217-218° C. (hexanes/ethyl acetate); $^1$H NMR (300 MHz, CDCl$_3$) δ 7.53 (d, J=8.1 Hz, 2H), 7.38-7.21 (m, 7H), 6.02 (t, J=5.6 Hz, 1H), 4.57 (d, J=5.6 Hz, 2H), 4.35-4.24 (m, 1H), 3.98-3.89 (m, 1H), 3.49-3.41 (m, 1H), 2.93-2.74 (m, 2H), 2.63 (s, 3H), 2.12-1.68 (m, 3H), 1.62-1.42 (m, 1H); $^{13}$C NMR (75 MHz, CDCl$_3$) δ 171.6, 162.6, 156.9, 152.1, 143.2, 137.9, 129.6, 128.8, 127.9, 127.7, 125.9, 125.5, 125.4, 119.9, 47.9, 44.1, 43.9, 37.3, 24.9, 21.3, 17.4; MS (ES+) m/z 488.1 (M+1).

Example 2.7

Synthesis of N-benzyl-4-methyl-2-(3-(4-methylbenzyl)-2-oxopiperidin-1-yl)thiazole-5-carboxamide

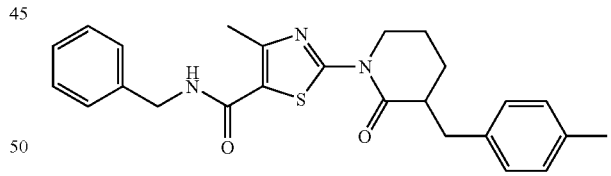

Following the procedure as described in Example 2, making variation as required to use N-benzyl-4-methyl-2-(2-oxopiperidin-1-yl)thiazole-5-carboxamide in place of N-(4-fluorobenzyl)-4-methyl-2-(2-oxopyrrolidin-1-yl)thiazole-5-carboxamide to react with 1-(bromomethyl)-4-methylbenzene in place of 1-(bromomethyl)-4-(trifluoromethyl)benzene, the title compound was obtained as a white solid in 53% yield: mp 110-113° C. (hexanes/ethyl acetate); $^1$H NMR (300 MHz, CDCl$_3$) δ 7.37-7.22 (m, 5H), 7.12-6.99 (m, 4H), 6.09 (t, J=5.6 Hz, 1H), 4.56 (d, J=5.6 Hz, 2H), 4.28-4.19 (m, 1H), 3.99-3.86 (m, 1H), 3.43-3.29 (m, 1H), 2.82-2.66 (m, 2H), 2.63 (s, 3H), 2.29 (s, 3H), 2.06-1.69 (m, 3H), 1.61-1.43 (m, 1H); $^{13}$C NMR (75 MHz, CDCl$_3$) δ 172.2, 162.7, 157.0, 152.1, 138.0, 136.1, 135.8, 129.2, 129.1, 128.8, 127.9, 127.6, 119.4, 48.1, 44.2, 44.0, 37.1, 24.8, 21.2, 21.1, 17.4; MS (ES+) m/z 434.3 (M+1).

Example 2.8

Synthesis of N-benzyl-2-(3-(3-fluorobenzyl)-2-oxopiperidin-1-yl)-4-methylthiazole-5-carboxamide

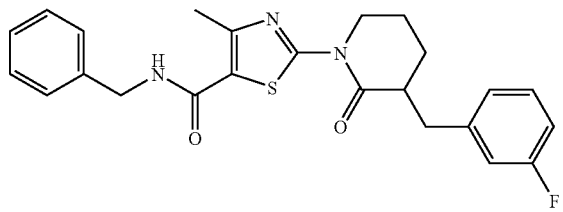

Following the procedure as described in Example 2, making variation as required to use N-benzyl-4-methyl-2-(2-oxopiperidin-1-yl)thiazole-5-carboxamide in place of N-(4-fluorobenzyl)-4-methyl-2-(2-oxopyrrolidin-1-yl)thiazole-5-carboxamide to react with 1-(bromomethyl)-3-fluorobenzene in place of 1-(bromomethyl)-4-(trifluoromethyl)benzene, the title compound was obtained as a white solid in 89% yield: mp 170-171° C. (hexanes/ethyl acetate); $^1$H NMR (300 MHz, CDCl$_3$) δ 7.39-7.17 (m, 6H), 6.99-6.89 (m, 3H), 6.01 (t, J=5.5 Hz, 1H), 4.57 (d, J=5.5 Hz, 2H), 4.33-4.21 (m, 1H), 3.99-3.89 (m, 1H), 3.45-3.36 (m, 1H), 3.86-3.27 (m, 2H), 2.63 (s, 3H), 2.10-1.96 (m, 1H), 1.94-1.73 (m, 2H), 1.61-1.43 (m, 1H); $^{13}$C NMR (75 MHz, CDCl$_3$) δ 171.8, 162.9, 162.6, 156.9, 152.1, 141.6, 137.9, 130.1, 128.8, 127.9, 127.7, 124.9, 119.5, 114.9, 114.6, 113.6, 48.0, 44.0, 37.3, 24.9, 21.3, 17.4; MS (ES+) m/z 438.2 (M+1).

Example 2.9

Synthesis of N-benzyl-2-(3-(4-methoxybenzyl)-2-oxopiperidin-1-yl)-4-methylthiazole-5-carboxamide

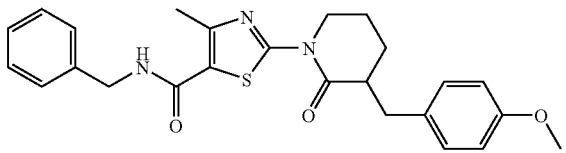

Following the procedure as described in Example 2, making variation as required to use N-benzyl-4-methyl-2-(2-oxopiperidin-1-yl)thiazole-5-carboxamide in place of N-(4-fluorobenzyl)-4-methyl-2-(2-oxopyrrolidin-1-yl)thiazole-5-carboxamide to react with 1-(bromomethyl)-4-methoxybenzene in place of 1-(bromomethyl)-4-(trifluoromethyl)benzene, the title compound was obtained as a white solid in 28% yield: mp 116-118° C. (hexanes/ethyl acetate); $^1$H NMR (300 MHz, CDCl$_3$) δ 7.39-7.23 (m, 5H), 7.08 (d, J=8.5 Hz, 2H), 6.80 (d, J=8.5 Hz, 2H), 6.00 (t, J=5.6 Hz, 1H), 4.57 (d, J=5.6 Hz, 2H), 4.29-4.20 (m, 1H), 3.97-3.88 (m, 1H), 3.76 (s, 3H), 3.37-3.27 (m, 1H), 2.82-2.67 (m, 2H), 2.63 (s, 3H), 2.08-1.93 (m, 1H), 1.92-1.71 (m, 2H), 1.62-1.44 (m, 1H); $^{13}$C NMR (75 MHz, CDCl$_3$) δ 166.3, 156.7, 152.3, 151.1, 146.2, 131.9, 124.9, 124.2, 122.9, 121.9, 121.7, 113.4, 107.9, 49.3, 42.2, 38.3, 38.1, 30.7, 18.8, 15.3, 11.4; MS (ES+) m/z 450.2 (M+1).

Example 2.10

Synthesis of N-benzyl-2-(3-(2,5-difluorobenzyl)-2-oxopiperidin-1-yl)-4-methylthiazole-5-carboxamide

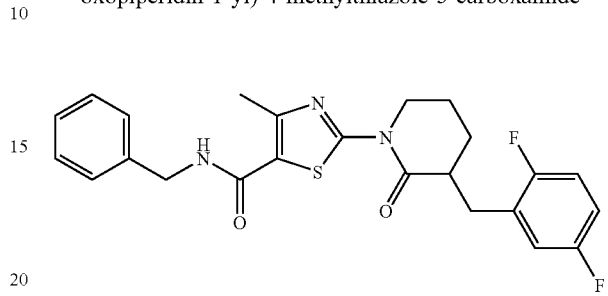

Following the procedure as described in Example 2, making variation as required to use N-benzyl-4-methyl-2-(2-oxopiperidin-1-yl)thiazole-5-carboxamide in place of N-(4-fluorobenzyl)-4-methyl-2-(2-oxopyrrolidin-1-yl)thiazole-5-carboxamide to react with 2-(bromomethyl)-1,4-difluorobenzene in place of 1-(bromomethyl)-4-(trifluoromethyl)benzene, the title compound was obtained as a white solid in 32% yield: mp 144-145° C. (hexanes/ethyl acetate); $^1$H NMR (300 MHz, CDCl$_3$) δ 7.37-7.22 (m, 5H), 7.02-6.81 (m, 3H), 6.01 (t, J=5.6 Hz, 1H), 4.56 (d, J=5.6 Hz, 2H), 4.32-4.20 (m, 1H), 4.03-3.94 (m, 1H), 3.47-3.37 (m, 1H), 2.90-2.73 (m, 2H), 2.63 (s, 3H), 2.12-1.98 (m, 1H), 1.96-1.75 (m, 2H), 1.64-1.45 (m, 1H); $^{13}$C NMR (75 MHz, CDCl$_3$) δ 171.5, 162.6, 160.2, 158.6, 157.3, 156.9, 152.2, 137.9, 128.8, 127.9, 127.5, 119.6, 117.7, 116.3, 114.7, 47.9, 44.1, 43.0, 30.6, 24.9, 21.3, 17.3; MS (ES+) m/z 456.2 (M+1).

Example 2.11

Synthesis of N-benzyl-2-(3-benzyl-2-oxopiperidin-1-yl)-4-methylthiazole-5-carboxamide

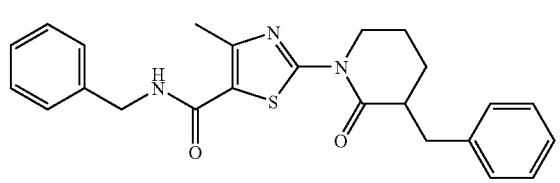

Following the procedure as described in Example 2, making variation as required to use N-benzyl-4-methyl-2-(2-oxopiperidin-1-yl)thiazole-5-carboxamide in place of N-(4-fluorobenzyl)-4-methyl-2-(2-oxopyrrolidin-1-yl)thiazole-5-carboxamide to react with (bromomethyl)benzene in place of 1-(bromomethyl)-4-(trifluoromethyl)benzene, the title compound was obtained as a white solid in 26% yield: mp 162-164° C. (hexanes/ethyl acetate); $^1$H NMR (300 MHz, CDCl$_3$) δ 7.39-7.32 (m, 10H), 6.01 (br s, 1H), 4.57 (d, J=5.3 Hz, 2H), 4.32-4.18 (m, 1H), 4.02-3.88 (m, 1H), 3.47-3.38 (m, 1H), 2.87-2.69 (m, 2H), 2.64 (s, 3H), 2.07-1.45 (m, 4H); $^{13}$C NMR (75 MHz, CDCl$_3$) δ 172.2, 162.7, 157.0, 152.2, 138.9, 137.9, 129.2, 128.8, 128.6, 127.9, 127.7, 126.5, 119.4, 48.1, 44.1, 44.0, 37.6, 24.8, 21.2, 17.4; MS (ES+) m/z 420.5 (M+1).

Example 2.12

Synthesis of N-benzyl-2-(3-(4-fluorobenzyl)-2-oxopiperidin-1-yl)-4-methylthiazole-5-carboxamide

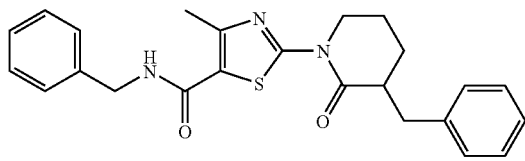

Following the procedure as described in Example 2, making variation as required to use N-benzyl-4-methyl-2-(2-oxopiperidin-1-yl)thiazole-5-carboxamide in place of N-(4-fluorobenzyl)-4-methyl-2-(2-oxopyrrolidin-1-yl)thiazole-5-carboxamide to react with 1-(bromomethyl)-4-fluorobenzene in place of 1-(bromomethyl)-4-(trifluoromethyl)benzene, the title compound was obtained as a white solid in 61% yield: mp 154-155° C. (hexanes/ethyl acetate); $^1$H NMR (300 MHz, CDCl$_3$) δ 7.34-7.21 (m, 5H), 7.12-7.07 (m, 2H), 6.99-6.88 (m, 2H), 6.16 (t, J=5.6 Hz, 1H), 4.55 (d, J=5.6 Hz, 2H), 4.29-4.16 (m, 1H), 3.97-3.82 (m, 1H), 3.39-3.25 (m, 1H), 2.82-2.66 (m, 2H), 2.61 (s, 3H), 2.06-1.91 (m, 1H), 1.89-1.69 (m, 2H), 1.57-1.41 (m, 1H); $^{13}$C NMR (75 MHz, CDCl$_3$) δ 171.9, 162.7, 161.6, 156.9, 151.9, 138.0, 134.6, 130.6, 128.8, 127.9, 127.6, 119.6, 115.3, 48.0, 44.1, 44.0, 36.7, 24.8, 21.2, 17.4; MS (ES+) m/z 438.2 (M+1).

Example 2.13

Synthesis of N-(3-fluorobenzyl)-2-(3-(4-fluorobenzyl)-2-oxopiperidin-1-yl)-4-methylthiazole-5-carboxamide

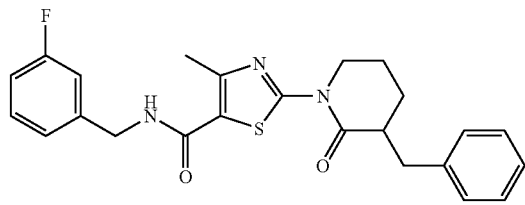

Following the procedure as described in Example 2, making variation as required to use N-(3-fluorobenzyl)-4-methyl-2-(2-oxopiperidin-1-yl)thiazole-5-carboxamide in place of N-(4-fluorobenzyl)-4-methyl-2-(2-oxopyrrolidin-1-yl)thiazole-5-carboxamide to react with 1-(bromomethyl)-4-fluorobenzene in place of 1-(bromomethyl)-4-(trifluoromethyl)benzene, the title compound was obtained as a white solid in 46% yield: mp 173-175° C. (hexanes/ethyl acetate); $^1$H NMR (300 MHz, CDCl$_3$) δ 7.31-7.24 (m, 1H), 7.15-6.88 (m, 7H), 6.12 (t, J=5.6 Hz, 1H), 4.55 (d, J=5.6 Hz, 2H), 4.29-4.21 (m, 1H), 3.98-3.86 (m, 1H), 3.40-3.27 (m, 1H), 2.86-2.69 (m, 2H), 2.62 (s, 3H), 2.08-1.95 (m, 1H), 1.93-1.73 (m, 2H), 1.61-1.44 (m, 1H); $^{13}$C NMR (75 MHz, CDCl$_3$) δ 171.9, 162.9, 162.6, 161.6, 156.9, 152.4, 140.6, 134.5, 130.5, 130.2, 123.2, 119.1, 115.3, 114.6, 114.4, 47.9, 44.1, 43.4, 36.6, 24.8, 21.2, 17.3; MS (ES+) m/z 456.3 (M+1).

Example 2.14

Synthesis of N-(3-fluorobenzyl)-4-methyl-2-(2-oxo-3-(4-(trifluoromethyl)benzyl)piperidin-1-yl)thiazole-5-carboxamide

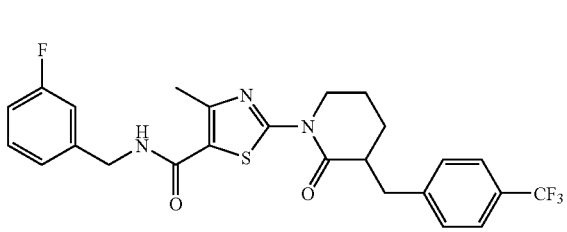

Following the procedure as described in Example 2, making variation as required to use N-(3-fluorobenzyl)-4-methyl-2-(2-oxopiperidin-1-yl)thiazole-5-carboxamide in place of N-(4-fluorobenzyl)-4-methyl-2-(2-oxopyrrolidin-1-yl)thiazole-5-carboxamide to react with 1-(bromomethyl)-4-(trifluoromethyl)benzene, the title compound was obtained as a white solid in 41% yield: mp 177-178° C. (hexanes/ethyl acetate); $^1$H NMR (300 MHz, CDCl$_3$) δ 7.52 (d, J=8.1 Hz, 2H), 7.30-7.27 (m, 3H), 7.10-6.92 (m, 3H), 6.11 (t, J=5.6 Hz, 1H), 4.56 (d, J=5.6 Hz, 2H), 4.33-4.21 (m, 1H), 4.00-3.88 (m, 1H), 3.53-3.56 (m, 1H), 2.94-2.73 (m, 2H), 2.62 (s, 3H), 2.11-1.95 (m, 1H), 1.94-1.75 (m, 2H), 1.62-1.43 (m, 1H); $^{13}$C NMR (75 MHz, CDCl$_3$) δ 171.7, 162.9, 162.7, 156.9, 152.4, 143.2, 140.6, 130.3, 129.6, 128.9, 125.9, 125.5, 125.4, 123.3, 122.4, 119.3, 114.7, 114.5, 48.0, 43.9, 43.3, 37.3, 24.9, 21.3, 17.4; MS (ES+) m/z 506.3 (M+1).

Example 3

Synthesis of 2-(3-(cyclopropylmethyl)-2-oxopyrrolidin-1-yl)-N-(4-fluorobenzyl)-4-methylthiazole-5-carboxamide

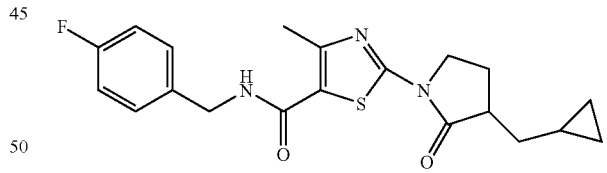

To a solution of N-(4-fluorobenzyl)-4-methyl-2-(2-oxopyrrolidin-1-yl)thiazole-5-carboxamide (0.13 g, 0.38 mmol) in a mixture of anhydrous tetrahydrofuran and 1,3-dimethyl-3,4,5,6-tetrahydro-2(1H)-pyrimidinone (8/1, v/v) at −78° C. was added lithium bis(trimethylsilyl)amide in tetrahydrofuran (0.83 mL, 0.83 mmol) dropwise. The reaction mixture was stirred at −78° C. for 5 minutes, followed by the addition of cyclopropanecarbaldehyde (0.028 mL, 0.38 mmol) dropwise. The reaction mixture was warmed to ambient temperature after 3 hours followed by the addition of aqueous saturated ammonium chloride (10 mL) solution. The mixture was extracted with dichloromethane (3×10 mL). The combined organic solutions were dried over anhydrous sodium sulfate, filtered and concentrated in vacuo. The residue was dissolved in ethyl acetate and hydrogenated in the presence of catalytic amount of Pd/C (20% w/w) at ambient temperature and atmospheric pressure for 1 hour. The reaction mixture was filtered through a bed of celite and the filtrate was concentrated in vacuo. The residue was purified by column chromatography (ethyl acetate/hexanes (1/1)) to afford the title compound as a white solid (0.025 g, 17%): mp 153-155° C. (hexanes/ethyl acetate); $^1$H NMR (300 MHz, CDCl$_3$) δ 7.34-7.23 (m, 2H), 7.01 (t, J=8.6 Hz, 2H), 5.95 (t, J=5.6 Hz, 1H), 4.52 (d, J=5.6 Hz, 2H), 4.23-4.14 (m, 1H), 3.99-3.90 (m, 1H), 2.87-2.78 (m, 1H), 2.62 (s, 3H), 2.53-2.42 (m, 1H), 2.08-1.94 (m, 1H), 1.79-1.69 (m, 1H), 1.52-1.42 (m, 1H), 0.84-0.69 (m, 1H), 0.53-0.39 (m, 2H), 0.16-0.03 (m, 2H); $^{13}$C NMR (75 MHz, CDCl$_3$) δ 175.9, 162.4, 162.3, 155.5, 152.9, 133.7, 129.6, 118.2, 115.7, 46.2, 43.3, 35.5, 24.9, 17.3, 8.6, 4.8, 4.3; MS (ES+) m/z 388.2 (M+1).

Example 3.1

Synthesis of N-benzyl-4-methyl-2-(2-oxo-3-phenethylpiperidin-1-yl)thiazole-5-carboxamide

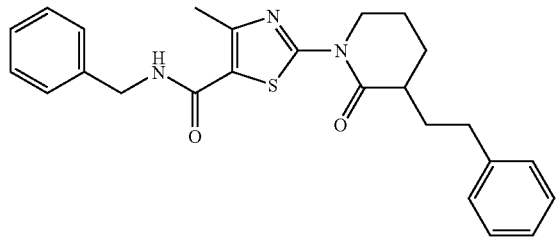

Following the procedure as described in Example 3, making variations as required to use 2-phenylacetaldehyde in place of cyclopropanecarbaldehyde to react with N-benzyl-4-methyl-2-(2-oxopiperidin-1-yl)thiazole-5-carboxamide in place of N-(4-fluorobenzyl)-4-methyl-2-(2-oxopyrrolidin-1-yl)thiazole-5-carboxamide, the title compound was obtained as a white solid in 24% yield: mp 124-126° C. (hexanes/ethyl acetate); $^1$H NMR (300 MHz, CDCl$_3$) δ 7.46-7.09 (m, 10H), 5.98 (t, J=5.4 Hz, 1H), 4.55 (d, J=5.4 Hz, 2H), 4.29-4.20 (m, 1H), 4.07-4.04 (m, 1H), 2.83-2.66 (m, 2H), 2.64 (s, 3H), 2.61-2.48 (m, 1H), 2.41-2.26 (m, 1H), 2.17-2.01 (m, 2H), 1.96-1.76 (m, 2H), 1.74-1.58 (m, 1H); $^{13}$C NMR (75 MHz, CDCl$_3$) δ 172.8, 162.7, 156.9, 152.2, 141.3, 137.9, 128.8, 128.5, 128.4, 127.9, 127.6, 126.1, 119.1, 47.9, 44.1, 41.4, 33.3, 33.0, 25.7, 21.3, 17.4; MS (ES+) m/z 434.1 (M+1).

Example 3.2

Synthesis of N-benzyl-4-methyl-2-(2-oxo-3-(3-phenylpropyl)piperidin-1-yl)thiazole-5-carboxamide

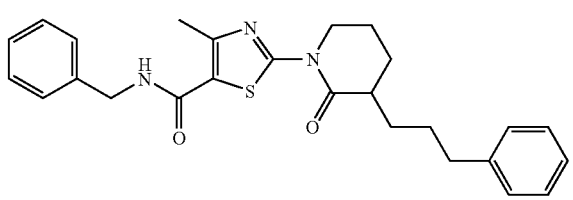

Following the procedure as described in Example 3, making variations as required to use 3-phenylpropanal in place of cyclopropanecarbaldehyde to react with N-benzyl-4-methyl-2-(2-oxopiperidin-1-yl)thiazole-5-carboxamide in place of N-(4-fluorobenzyl)-4-methyl-2-(2-oxopyrrolidin-1-yl)thiazole-5-carboxamide, the title compound was obtained as a white solid in 10% yield: mp 140-141° C. (hexanes/ethyl acetate); $^1$H NMR (300 MHz, CDCl$_3$) δ 7.37-7.10 (m, 10H), 5.98 (t, J=4.7 Hz, 1H), 4.55 (d, J=5.3 Hz, 2H), 4.31-4.19 (m, 1H), 4.04-3.91 (m, 1H), 2.69-2.47 (m, 6H), 2.11-1.78 (m, 4H), 1.76-1.53 (m, 4H); $^{13}$C NMR (75 MHz, CDCl$_3$) δ 172.8, 162.7, 157.0, 152.2, 142.0, 137.9, 128.8, 128.4, 128.3, 127.9, 127.6, 125.9, 119.2, 47.9, 44.1, 42.2, 35.9, 31.4, 28.9, 25.5, 21.3, 17.4; MS (ES+) m/z 448.21 (M+1).

Example 4

Synthesis of 2-(3-bromo-2-oxopyrrolidin-1-yl)-N-(4-fluorobenzyl)-4-methylthiazole-5-carboxamide

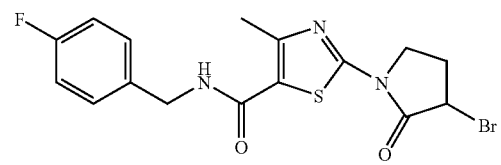

To a solution of N-(4-fluorobenzyl)-4-methyl-2-(2-oxopyrrolidin-1-yl)thiazole-5-carboxamide (0.35 g, 1.05 mmol) in anhydrous tetrahydrofuran (25 mL) at −78° C. was added lithium bis(trimethylsilyl)amide in tetrahydrofuran (2.31 mL, 2.31 mmol) dropwise. The reaction mixture was stirred at −78° C. for 5 minutes, followed by the addition of N-bromosuccinimide (0.19 g, 1.05 mmol) dropwise. The reaction mixture was stirred at −78° C. for 10 min, quenched with aqueous saturated ammonium chloride solution (10 mL) and extracted with dichloromethane (3×10 mL). The combined organic solutions were dried over anhydrous sodium sulfate, filtered and concentrated in vacuo. The residue was purified by column chromatography eluting with ethyl acetate/hexanes (1/1) to afford the title compound as a white solid (0.22 g, 51%): $^1$H NMR (300 MHz, CDCl$_3$) δ 7.34-7.24 (m, 2H), 7.07-6.97 (m, 2H), 5.98 (b s, 1H), 4.66-4.59 (m, 1H), 4.58 (d, J=5.8 Hz, 2H), 4.30-4.14 (m, 1H), 2.86-2.69 (m, 1H), 2.64 (s, 3H), 2.56-2.45 (m, 1H); MS (ES+) m/z 412 (M+1), 414 (M+1).

Example 4.1

Synthesis of N-benzyl-2-(3-bromo-2-oxopiperidin-1-yl)-4-methylthiazole-5-carboxamide

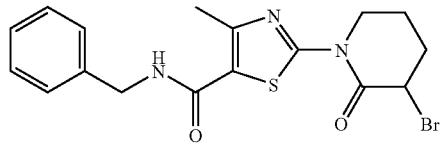

Following the procedure as described in Example 4, making variations as required to use N-benzyl-4-methyl-2-(2-oxopiperidin-1-yl)thiazole-5-carboxamide in place of N-(4-fluorobenzyl)-4-methyl-2-(2-oxopyrrolidin-1-yl)thiazole-5-carboxamide to react with N-bromosuccinimide, the title compound was obtained as a yellow oil in 56% yield: MS (ES+) m/z 408.2 (M+1), 410.2 (M+1).

Example 5

Synthesis of 2-(3-(2-cyclopropylethylamino)-2-oxopyrrolidin-1-yl)-N-(4-fluorobenzyl)-4-methylthiazole-5-carboxamide

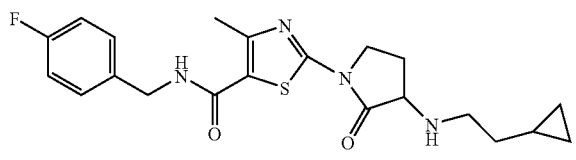

To a solution of 2-(3-bromo-2-oxopyrrolidin-1-yl)-N-(4-fluorobenzyl)-4-methylthiazole-5-carboxamide (0.050 g, 0.12 mmol) in a mixture of tetrahydrofuran and water (1/0.1, v/v) was added potassium carbonate (0.034 g, 0.24 mmol) and 2-cyclopropylethanamine (0.012 g, 0.15 mmol). The reaction mixture was stirred at ambient temperature for 17 hours and concentrated in vacuo. The residue was purified by column chromatography (ethyl acetate/hexanes (3/1)) to afford the title compound as a white solid (0.030 g, 60%): mp 151-152° C. (hexanes/ethyl acetate); $^1$H NMR (300 MHz, CDCl$_3$) δ 7.32-7.22 (m, 2H), 7.05-6.96 (m, 2H), 6.01 (t, J=5.6 Hz, 1H), 4.51 (d, J=5.6 Hz, 2H), 4.27-4.17 (m, 1H), 3.93-3.81 (m, 1H), 3.76-3.66 (m, 1H), 2.88-2.67 (m, 2H), 2.61 (s, 3H), 2.58-2.44 (m, 1H), 2.10-1.91 (m, 1H), 1.52-1.29 (m, 2H), 0.75-0.59 (m, 1H), 0.49-0.37 (m, 2H), 0.08-0.01 (m, 2H); $^{13}$C NMR (75 MHz, CDCl$_3$) δ 173.6, 162.3, 162.2, 155.2, 152.9, 133.7, 129.6, 118.6, 115.6, 59.5, 47.9, 44.9, 43.4, 35.0, 26.9, 17.3, 8.8, 4.4, 4.2; MS (ES+) m/z 417.3 (M+1).

Example 5.1

Synthesis of N-(4-fluorobenzyl)-2-(3-(4-fluorobenzylamino)-2-oxopyrrolidin-1-yl)-4-methylthiazole-5-carboxamide

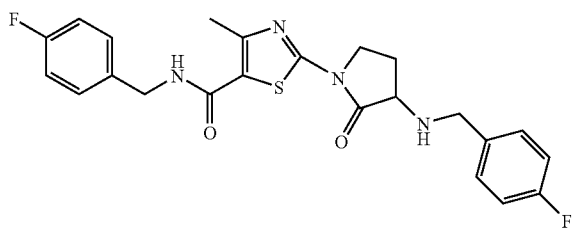

Following the procedure as described in Example 5, making variation as required to use (4-fluorophenyl)methanamine in place of 2-cyclopropylethanamine to react with 2-(3-bromo-2-oxopyrrolidin-1-yl)-N-(4-fluorobenzyl)-4-methylthiazole-5-carboxamide, the title compound was obtained as a white solid in 85% yield: mp 123-124° C. (hexanes/ethyl acetate); $^1$H NMR (300 MHz, CDCl$_3$) δ 7.35-7.21 (m, 4H), 7.06-6.92 (m, 4H), 6.07 (t, J=5.6 Hz, 1H), 4.50 (d, J=5.6 Hz, 2H), 4.20 (t, J=5.6 Hz, 1H), 3.97-3.76 (m, 3H), 3.68 (t, J=8.6 Hz, 1H), 2.60 (s, 3H), 2.53-2.37 (m, 1H), 2.11-1.89 (m, 2H); $^{13}$C NMR (75 MHz, CDCl$_3$) δ 173.6, 162.3, 162.2, 162.1, 155.2, 152.8, 135.0, 133.7, 129.8, 129.6, 118.8, 115.6, 115.4, 58.5, 51.0, 44.8, 43.3, 27.1, 17.3; MS (ES+) m/z 457.3 (M+1).

Example 5.2

Synthesis of N-(4-fluorobenzyl)-4-methyl-2-(2-oxo-3-(3,3,3-trifluoropropylamino)pyrrolidin-1-yl)thiazole-5-carboxamide

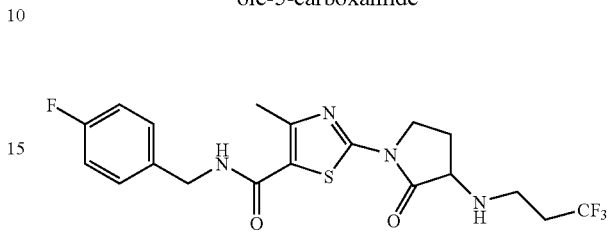

Following the procedure as described in Example 5, making variation as required to use 3,3,3-trifluoropropan-1-amine in place of 2-cyclopropylethanamine to react with 2-(3-bromo-2-oxopyrrolidin-1-yl)-N-(4-fluorobenzyl)-4-methylthiazole-5-carboxamide, the title compound was obtained as a white solid in 19% yield: mp 142-143° C. (hexanes/ethyl acetate); $^1$H NMR (300 MHz, CDCl$_3$) δ 7.35 (m, 2H), 7.07-6.93 (m, 2H), 6.00 (br s, 1H), 4.51 (d, J=5.4 Hz, 2H), 4.29-4.16 (m, 1H), 3.65-3.81 (m, 1H), 3.76-3.64 (m, 1H), 3.15-3.02 (m, 1H), 2.98-2.85 (m, 1H), 2.61 (s, 3H), 2.60-2.48 (m, 1H), 2.43-2.22 (m, 2H), 2.08-1.89 (m, 1H), 1.79 (br s, 1H); MS (ES+) m/z 445.3 (M+1).

Example 5.3

Synthesis of N-benzyl-4-methyl-2-(2-oxo-3-(4-(trifluoromethyl)benzylamino)piperidin-1-yl)thiazole-5-carboxamide

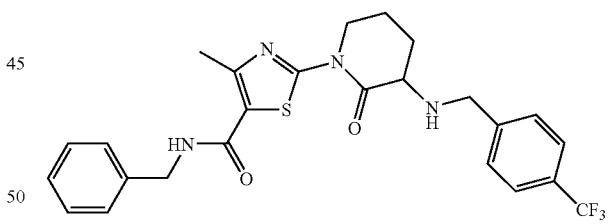

Following the procedure as described in Example 5, making variation as required to use (4-(trifluoromethyl)phenyl)methanamine in place of 2-cyclopropylethanamine to react with N-benzyl-2-(3-bromo-2-oxopiperidin-1-yl)-4-methylthiazole-5-carboxamide in place of 2-(3-bromo-2-oxopyrrolidin-1-yl)-N-(4-fluorobenzyl)-4-methylthiazole-5-carboxamide, the title compound was obtained as a white solid in 20% yield: mp 39-40° C. (diethyl ether); $^1$H NMR (300 MHz, CDCl$_3$) δ 7.55 (d, J=8.1 Hz, 2H), 7.45 (d, J=8.1 Hz, 2H), 7.39-7.21 (m, 5H), 6.03 (t, J=5.6 Hz, 1H), 4.55 (d, J=5.6 Hz, 2H), 4.32-4.21 (m, 1H), 4.06-3.96 (m, 1H), 3.93 (s, 2H), 3.50-3.39 (m, 1H), 2.62 (s, 3H), 2.30-2.05 (m, 2H), 1.99-1.83 (m, 2H), 1.81-1.66 (m, 1H); $^{13}$C NMR (75 MHz, CDCl$_3$) δ 171.4, 162.5, 156.6, 152.0, 143.8, 137.9, 129.4, 128.8, 128.3, 127.9, 127.7, 125.5, 125.4, 119.7, 57.9, 50.9, 47.5, 44.1, 26.5, 20.4, 17.4; MS (ES+) m/z 503.3 (M+1).

Example 5.4

Synthesis of N-benzyl-2-(3-(cyclopropylmethylamino)-2-oxopiperidin-1-yl)-4-methylthiazole-5-carboxamide

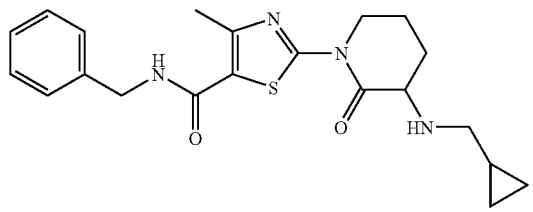

Following the procedure as described in Example 5, making variation as required to use cyclopropylmethanamine in place of 2-cyclopropylethanamine to react with N-benzyl-2-(3-bromo-2-oxopiperidin-1-yl)-4-methylthiazole-5-carboxamide in place of 2-(3-bromo-2-oxopyrrolidin-1-yl)-N-(4-fluorobenzyl)-4-methylthiazole-5-carboxamide, the title compound was obtained as a white solid in 69% yield: mp 125-126° C. (diethyl ether); $^1$H NMR (300 MHz, CDCl$_3$) δ 7.38-7.29 (m, 5H), 5.95 (t, J=5.5 Hz, 1H), 4.56 (d, J=5.5 Hz, 2H), 4.37-4.26 (m, 1H), 4.04-3.91 (m, 1H), 3.54-3.45 (m, 1H), 2.63 (s, 3H), 2.59-2.44 (m, 2H), 2.31-1.82 (m, 4H), 1.81-1.68 (m, 1H), 1.01-0.89 (m, 1H), 0.57-0.41 (m, 2H), 0.23-0.08 (m, 2H); $^{13}$C NMR (75 MHz, CDCl$_3$) δ 171.5, 162.5, 156.7, 152.2, 137.9, 128.8, 127.9, 127.7, 119.6, 58.5, 52.5, 47.6, 44.1, 26.4, 20.5, 17.4, 11.2, 3.6, 3.3; MS (ES+) m/z 399.3 (M+1).

Example 6

Synthesis of N-benzyl-2-(4-benzyl-2-oxopyrrolidin-1-yl)-4-methylthiazole-5-carboxamide

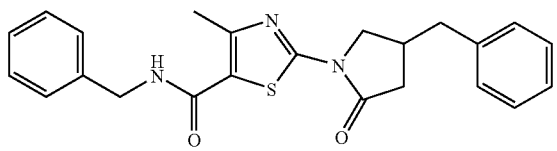

A mixture of 4-benzylpyrrolidin-2-one (0.068 g, 0.39 mmol), N-benzyl-2-bromo-4-methylthiazole-5-carboxamide (0.10 g, 0.32 mmol), cesium carbonate (0.16 g, 0.48 mmol), tris(dibenzylideneacetone)dipalladium(0) (0.006 g, 0.060 mmol) and xantphos (0.008 g, 0.013 mmol) in anhydrous toluene (3 mL) was subjected to microwave irradiation at 120° C. for 15 min. The reaction mixture was concentrated in vacuo and the residue was purified by column chromatography (ethyl acetate/hexanes (1/1)) to afford the title compound as a white solid (0.017 g, 13%): mp 143-144° C. (hexanes/ethyl acetate); $^1$H NMR (300 MHz, CDCl$_3$) δ 7.38-7.11 (m, 10H), 5.91 (br s, 1H), 4.56 (d, J=5.5 Hz, 2H), 4.25-4.13 (m, 1H), 3.85-3.72 (m, 1H), 2.95-2.68 (m, 4H), 2.61 (s, 3H), 2.52-2.39 (m, 1H); $^{13}$C NMR (75 MHz, CDCl$_3$) δ 173.0, 162.3, 155.3, 152.6, 138.2, 137.9, 128.8, 128.7, 127.9, 127.6, 126.8, 118.6, 52.6, 44.0, 40.1, 37.7, 33.4, 17.2; MS (ES+) m/z 406.3 (M+1).

Example 7

Synthesis of (S)-N-benzyl-2-(4-hydroxy-2-oxopyrrolidin-1-yl)-4-methylthiazole-5-carboxamide

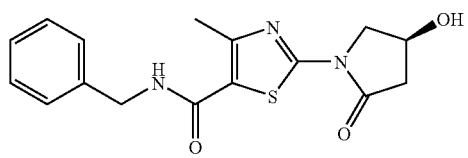

A. To a solution of (S)-4-hydroxypyrrolidin-2-one (1.00 g, 9.89 mmol) in anhydrous dichloromethane (40 mL) was added 3,4-dihydro-2H-pyrane (1.35 mL, 14.84 mmol) and pyridinium p-toluenesulfonate (0.25 g, 0.99 mmol). The reaction mixture was stirred at ambient temperature for 18 hours, diluted with diethyl ether (100 mL) and washed with brine (25 mL). The organic layer was dried over anhydrous sodium sulfate, filtered and concentrated to afford (4S)-4-(2-oxotetrahydro-2H-pyran-4-yloxy)pyrrolidin-2-one as a clear oil (1.20 g, 61%): $^1$H NMR (300 MHz, CDCl$_3$) δ 6.60 (br s, 1H), 4.98-4.57 (m, 1H), 4.57-4.46 (m, 1H), 3.89-3.70 (m, 1H), 3.68-3.22 (m, 3H), 2.69-2.22 (m, 2H), 1.89-1.50 (m, 6H).

B. A mixture of (4S)-4-(2-oxotetrahydro-2H-pyran-4-yloxy)pyrrolidin-2-one (0.036 g, 0.19 mmol), N-benzyl-2-bromo-4-methylthiazole-5-carboxamide (0.050 g, 0.16 mmol), cesium carbonate (0.079 g, 0.24 mmol), [1,1'-bis(diphenylphosphino)-ferrocene]dichloropalladium(II) complex with dichloromethane (1:1) (0.003 g, 0.003 mmol) and xantphos (0.004 g, 0.006 mmol) in anhydrous toluene (3 mL) was subjected to microwave irradiation at 80° C. for 20 min. The reaction mixture was diluted with ethyl acetate (10 mL) and washed with water (4 mL). The organic layer was dried over anhydrous sodium sulfate, filtered and concentrated in vacuo. The residue was dissolved in ethanol and a catalytic amount of pyridinium p-toluenesulfonate was added to the solution. The reaction mixture was heated at 50° C. for 6 hours and concentrated in vacuo. The residue was dissolved in dichloromethane (15 mL) and washed with water (5 mL). The organic layer was dried over anhydrous sodium sulfate, filtered and concentrated in vacuo. The obtained white solid was washed with diethyl ether (25 mL) and dried in air to afford the title compound (0.028 g, 53%): mp 203-204° C. (diethyl ether); $^1$H NMR (300 MHz, DMSO-d$_6$) δ 8.60 (t, J=6.0 Hz, 1H), 7.33-7.17 (m, 5H), 5.46 (d, J=3.8 Hz, 1H), 4.47-4.41 (m, 1H), 4.35 (d, J=6.0 Hz, 2H), 4.12-4.04 (m, 1H), 3.93-3.85 (m, 1H), 3.00-2.90 (m, 1H), 2.48 (s, 3H), 2.42-2.33 (m, 1H); $^{13}$C NMR (75 MHz, DMSO-d$_6$) δ 173.3, 162.1, 155.9, 140.0, 128.7, 127.7, 127.2, 119.4, 63.6, 57.0, 43.1, 41.7, 17.5; MS (ES+) m/z 332.2 (M+1).

Example 7.1

Synthesis of (R)-N-benzyl-2-(4-hydroxy-2-oxopyrrolidin-1-yl)-4-methylthiazole-5-carboxamide

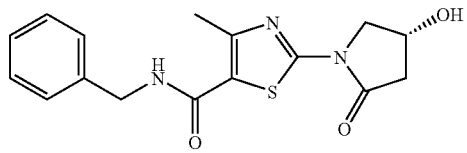

Following the procedure as described in Example 7, making variations as required to use (R)-4-hydroxypyrrolidin-2-one in place of (S)-4-hydroxypyrrolidin-2-one, the title compound was obtained as a white solid in 53% yield: mp 203-204° C. (diethyl ether); $^1$H NMR (300 MHz, DMSO-$d_6$) δ 8.60 (t, J=6.0 Hz, 1H), 7.33-7.17 (m, 5H), 5.46 (d, J=6.0 Hz, 1H), 4.48-4.40 (m, 1H), 4.35 (d, J=6.0 Hz, 2H), 4.12-4.04 (m, 1H), 3.93-3.85 (m, 1H), 3.00-2.90 (m, 1H), 2.48 (s, 3H), 2.42-2.33 (m, 1H); $^{13}$C NMR (75 MHz, DMSO-$d_6$) δ 173.3, 162.1, 155.9, 140.0, 128.7, 127.7, 127.2, 119.4, 63.6, 57.0, 43.1, 41.7, 17.5 MS (ES+) m/z 332.2 (M+1).

Example 8

Synthesis of 2-(3-(4-fluorobenzyl)-2-oxopyrrolidin-1-yl)-4-methyl-N-(pyridin-3-ylmethyl)thiazole-5-carboxamide

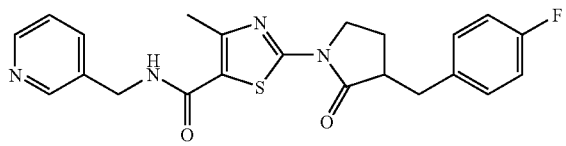

A mixture of 3-(4-fluorobenzyl)pyrrolidin-2-one (0.074 g, 0.39 mmol), 2-bromo-4-methyl-N-(pyridin-3-ylmethyl)thiazole-5-carboxamide (0.10 g, 0.32 mmol), cesium carbonate (0.16 g, 0.48 mmol), [1,1'-bis(diphenylphosphino)ferrocene]-dichloropalladium(II) complex with dichloromethane (1:1) (0.005 g, 0.006 mmol) and xantphos (0.007 g, 0.013 mmol) in anhydrous toluene (2 mL) was subjected to microwave irradiation at 80° C. for 35 min. The reaction mixture was concentrated in vacuo and the residue was purified by column chromatography (ethyl acetate/hexanes (3/1)) to afford the title compound as a white solid (0.045 g, 33%): mp 169-170° C. (hexanes/ethyl acetate); $^1$H NMR (300 MHz, CDCl$_3$) δ 8.59 (s, 1H), 8.52 (d, J=4.5 Hz, 1H), 7.68 (d, J=8.0 Hz, 1H), 7.30-7.23 (m, 1H), 7.14 (dd, J=8.0, 5.5 Hz, 2H), 6.95 (t, J=8.8 Hz, 2H), 6.16 (t, J=5.6 Hz, 1H), 4.59 (d, J=5.6 Hz, 2H), 4.07-3.95 (m, 1H), 3.92-3.79 (m, 1H), 3.20 (dd, J=13.9, 4.5 Hz, 1H), 3.07-2.93 (m, 1H), 2.83-2.74 (m, 1H), 2.61 (s, 3H), 2.32-2.18 (m, 1H), 1.98-1.82 (m, 1H); $^{13}$C NMR (75 MHz, CDCl$_3$) δ 174.8, 163.4, 162.5, 155.5, 153.2, 149.3, 149.1, 135.7, 133.8, 133.7, 130.4, 123.7, 118.2, 115.6, 45.9, 44.4, 41.5, 35.6, 24.2, 17.3; MS (ES+) m/z 425.3 (M+1).

Example 8.1

Synthesis of 4-methyl-2-(2-oxo-3-(4-(trifluoromethoxy)benzyl)pyrrolidin-1-yl)-N-(pyridin-3-ylmethyl)thiazole-5-carboxamide

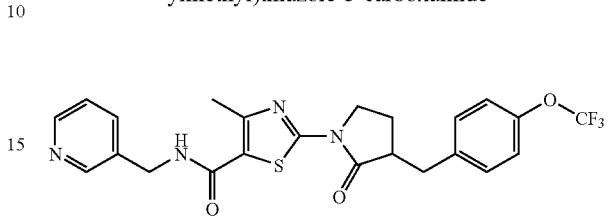

Following the procedure as described in Example 8, making variations as required to use 3-(4-(trifluoromethoxy)benzyl)pyrrolidin-2-one in place of 3-(4-fluorobenzyl)pyrrolidin-2-one to react with 2-bromo-4-methyl-N-(pyridin-3-ylmethyl)thiazole-5-carboxamide, the title compound was obtained as a white solid in 34% yield: mp 158-160° C. (hexanes/ethyl acetate); $^1$H NMR (300 MHz, CDCl$_3$) δ 8.58 (s, 1H), 8.49 (d, J=4.0 Hz, 1H), 7.68 (d, J=7.8 Hz, 1H), 7.31-7.06 (m, 5H), 6.43 (t, J=5.7 Hz, 1H), 4.58 (d, J=5.7 Hz, 2H), 4.06 (ddd, J=11.5, 8.0, 3.1 Hz, 1H), 3.86 (td, J=11.5, 8.0 Hz, 1H), 3.23 (dd, J=13.9, 4.4 Hz, 1H), 3.08-2.94 (m, 1H), 2.83-2.74 (m, 1H), 2.60 (s, 3H), 2.34-2.19 (m, 1H), 1.94-1.87 (m, 1H); $^{13}$C NMR (75 MHz, CDCl$_3$) δ 174.6, 162.5, 155.4, 153.2, 149.3, 148.9, 148.0, 138.1, 136.9, 135.7, 133.9, 130.3, 123.7, 121.2, 118.3, 45.9, 44.3, 41.5, 35.7, 24.3, 17.3; MS (ES+) m/z 491.3 (M+1).

Example 9

Synthesis of N-benzyl-2-(2,6-dioxo-4-phenylpiperidin-1-yl)-4-methylthiazole-5-carboxamide

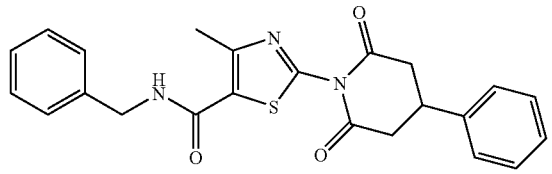

To a stirred solution of 2-amino-N-benzyl-4-methylthiazole-5-carboxamide (0.50 g, 2.0 mmol) in chloroform (15 mL) with triethylamine (1.8 mL, 10.0 mmol) was added 3-phenylpentanedioyl dichloride (0.45 g, 1.84 mmol). The mixture was stirred at ambient temperature for 2 h, washed with 20% hydrochloric acid solution (20 mL), dried over anhydrous sodium sulfate and filtered. The filtrate was concentrated in vacuo and the residue was crystallized from ethyl acetate/hexane to afford a solid, which was washed with cold methanol and dried in air to afford the title compound (0.46 g, 60%): $^1$H NMR (300 MHz, CDCl$_3$) δ 7.50-7.20 (m, 10H), 6.07 (br s, 1H), 4.60 (d, J=5.6 Hz, 2H), 3.60-3.50 (m, 1H), 3.13 (dd, J=17.1, 4.2 Hz, 2H), 2.95 (dd, J=17.1, 12.0 Hz, 2H), 2.68 (s, 3H); MS (ES+) m/z 420.1 (M+1).

Example 10

Synthesis of N-benzyl-2-(3-(hydroxy(phenyl)methyl)-2-oxopiperidin-1-yl)-4-methylthiazole-5-carboxamide

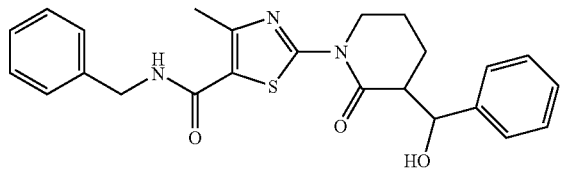

To a solution of N-benzyl-4-methyl-2-(2-oxopiperidin-1-yl)thiazole-5-carboxamide (0.25 g, 0.76 mmol) in anhydrous tetrahydrofuran (10 mL) at −78° C. was added lithium bis(trimethylsilyl)amide in tetrahydrofuran (0.83 mL, 0.83 mmol) dropwise. The reaction mixture was stirred at −78° C. for 5 minutes, followed by the dropwise addition of benzaldehyde (0.077 mL, 0.76 mmol). The resulting mixture was slowly warmed to −30° C. over 30 minutes, followed by the addition of water (5 mL) and extraction with dichloromethane (3×10 mL). The combined organic solution was dried over anhydrous sodium sulfate and filtered. The filtrate was concentrated in vacuo and the residue was purified by column chromatography (ethyl acetate/hexanes (1/1)) to afford the title compound as a white solid (0.010 g, 3%): mp 74-75° C. (hexanes/ethyl acetate); $^1$H NMR (300 MHz, CDCl$_3$) δ 7.42-7.22 (m, 10H), 6.01 (t, J=5.5 Hz, 1H), 5.63 (d, J=2.5 Hz, 1H), 4.57 (d, J=5.5 Hz, 2H), 4.38-4.30 (m, 1H), 3.91-3.81 (m, 1H), 2.88-2.82 (m, 1H), 2.63 (s, 3H), 2.09-1.51 (m, 4H); $^{13}$C NMR (75 MHz, CDCl$_3$) δ 171.7, 162.6, 152.0, 141.4, 137.9, 128.8, 128.6, 128.4, 127.9, 127.7, 127.5, 125.8, 119.7, 72.7, 49.8, 48.0, 44.1, 21.6, 19.4, 17.3; MS (ES+) m/z 436.2 (M+1).

Example 10.1

Synthesis of N-benzyl-2-(3-((5-ethylthiophen-2-yl)methylene)-2-oxopiperidin-1-yl)-4-methylthiazole-5-carboxamide

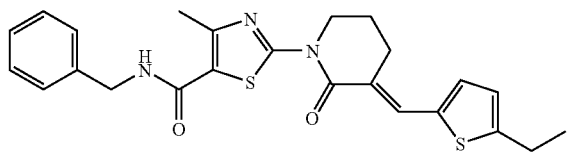

Following the procedure as described in Example 10, making variations as required to use 5-ethylthiophene-2-carbaldehyde in place of benzaldehyde to react with N-benzyl-4-methyl-2-(2-oxopiperidin-1-yl)thiazole-5-carboxamide, the title compound was obtained as a white solid in 14% yield: mp 171-172° C. (hexanes/ethyl acetate); $^1$H NMR (300 MHz, CDCl$_3$) δ 8.05 (s, 1H), 7.42-7.22 (m, 5H), 7.16 (d, J=3.7 Hz, 1H), 6.83 (dd, J=0.7, 3.7 Hz, 1H), 5.98 (t, J=5.5 Hz, 1H), 4.57 (d, J=5.5 Hz, 2H), 4.32-4.25 (m, 2H), 2.93-2.81 (m, 4H), 2.65 (s, 3H), 2.15-2.02 (m, 2H), 1.32 (t, J=7.5 Hz, 3H); $^{13}$C NMR (75 MHz, CDCl$_3$) δ 164.8, 162.7, 157.5, 153.7, 152.4, 137.9, 136.4, 133.6, 132.9, 128.8, 127.9, 127.6, 124.5, 122.7, 119.5, 46.9, 44.1, 25.9, 23.8, 21.9, 17.4, 15.7; MS (ES+) m/z 452.1 (M+1).

Example 10.2

Synthesis of N-benzyl-4-methyl-2-(2-oxo-3-(pyridin-3-ylmethylene)piperidin-1-yl)thiazole-5-carboxamide

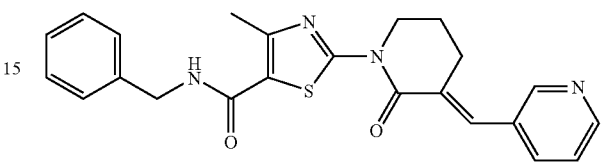

Following the procedure as described in Example 10, making variations as required to use nicotinaldehyde in place of benzaldehyde to react with N-benzyl-4-methyl-2-(2-oxopiperidin-1-yl)thiazole-5-carboxamide, the title compound was obtained as a white solid in 17% yield: mp 206-208° C. (ethyl acetate); $^1$H NMR (300 MHz, CDCl$_3$) δ 8.69 (br s, 1H), 8.54 (br s, 1H), 7.91 (s, 1H), 7.69 (d, J=7.8 Hz, 1H), 7.39-7.21 (m, 6H), 6.26 (t, J=5.5 Hz, 1H), 4.57 (d, J=5.5 Hz, 2H), 4.32-4.22 (m, 2H), 2.93-2.82 (m, 2H), 2.64 (s, 3H), 2.09-1.96 (m, 2H); $^{13}$C NMR (75 MHz, CDCl$_3$) δ 163.8, 162.6, 157.3, 152.3, 150.7, 149.4, 138.0, 136.8, 135.5, 130.5, 128.8, 127.9, 127.6, 123.5, 120.1, 47.4, 44.0, 25.9, 22.2, 17.4; MS (ES+) m/z 419.2 (M+1).

Example 11

Synthesis of N-benzyl-4-methyl-2-(2-oxo-3-(pyridin-3-ylmethyl)piperidin-1-yl)thiazole-5-carboxamide

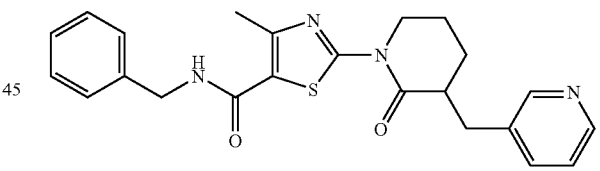

A solution of N-benzyl-4-methyl-2-(2-oxo-3-(pyridin-3-ylmethylene)piperidin-1-yl)thiazole-5-carboxamide (0.024 g, 0.053 mmol) in ethyl acetate (10 mL) was hydrogenated in the presence of catalytic amount of palladium on carbon (20% w/w) at ambient temperature and under atmospheric pressure for 3 hours. The reaction mixture was filtered through a bed of celite and the filtrate was concentrated in vacuo. The residue was recrystallized from hexanes/ethyl acetate to afford the title compound as a yellow solid (0.022 g, 92%): mp 140-141° C. (hexanes/ethyl acetate); $^1$H NMR (300 MHz, CDCl$_3$) δ 8.44 (br s, 2H), 7.51 (d, J=7.8 Hz, 1H), 7.42-7.16 (m, 6H), 6.07 (br s, 1H), 4.57 (d, J=5.6 Hz, 2H), 4.33-4.21 (m, 1H), 3.98-3.86 (m, 1H), 3.43-3.29 (m, 1H), 3.91-3.73 (m, 2H), 2.62 (s, 3H), 2.11-2.98 (m, 1H), 1.96-1.74 (m, 2H), 1.62-1.45 (m, 1H); $^{13}$C NMR (75 MHz, CDCl$_3$) δ 171.5, 162.6, 156.8, 152.1, 150.4, 147.9, 137.9, 136.9, 128.8, 128.7, 127.9, 127.6, 123.6, 119.6, 47.9, 44.1, 43.8, 34.6, 24.9, 21.3, 17.4; MS (ES+) m/z 421.1 (M+1).

Example 12

Measuring Stearoyl-CoA Desaturase Inhibition Activity of a Test Compound Using Mouse Liver Microsomes The identification of compounds of the invention as SCD inhibitors was readily accomplished using the SCD microsomal assay procedure described in Shanklin J. and Summerville C., *Proc. Natl. Acad. Sci. USA* (1991), Vol. 88, pp. 2510-2514.

Preparation of Mouse Liver Microsomes:

Male ICR outbread mice, on a high-carbohydrate, low fat diet, under light halothane (15% in mineral oil) anesthesia are sacrificed by exsanguination during periods of high enzyme activity. Livers are immediately rinsed with cold 0.9% NaCl solution, weighed and minced with scissors. All procedures are performed at 4° C. unless specified otherwise. Livers are homogenized in a solution (1/3 w/v) containing 0.25 M sucrose, 62 mM potassium phosphate buffer (pH 7.0), 0.15 M KCl, 15 mM N-acetyleysteine, 5 mM $MgCl_2$, and 0.1 mM EDTA using 4 strokes of a Potter-Elvehjem tissue homogenizer. The homogenate is centrifuged at 10,400×g for 20 min to eliminate mitochondria and cellular debris. The supernatant is filtered through a 3-layer cheesecloth and centrifuged at 105,000×g for 60 min. The microsomal pellet is gently resuspended in the same homogenization solution with a small glass/teflon homogenizer and stored at −70° C. The absence of mitochondrial contamination is enzymatically assessed. The protein concentration is measured using bovine serum albumin as the standard.

Incubation of Mouse Liver Microsomes with Test Compounds:

Desaturase activity is measured as the release of $^3H_2O$ from [9,10-$^3$H]stearoyl-CoA. Reactions per assay point conditions are as follows: 2 µL 1.5 mM stearoyl-CoA, 0.25 µL 1 mCi/mL $^3$H stearoyl CoA, 10 µL 20 mM NADH, 36.75 µL 0.1 M PK buffer ($K_2HPO_4/NaH_2PO_4$, pH 7.2). The test compound or control solution is added in a 1 µL volume. Reactions are started by adding 50 µL of microsomes (1.25 mg/mL). The plates are mixed and after 15 min incubation on a heating block (25° C.), the reactions are stopped by the addition of 10 µL 60% PCA. An aliquot of 100 µL is then transferred to a filter plate pretreated with charcoal and the plate centrifuged at 4000 rpm for 1 min. The flow through containing the $^3H_2O$ released by the SCD1 desaturation reaction is added to scintillation fluid and the radioactivity measured in a Packard TopCount. The data is analysed to identify the $IC_{50}$ for test compounds and reference compounds. Representative compounds of the invention showed activity as inhibitors of SCD when tested in this assay. The activity was defined in terms of % SCD enzyme activity remaining at the desired concentration of the test compound or as the $IC_{50}$ concentration.

The $IC_{50}$ (affinity) of the example compounds toward the stearoyl-CoA desaturase is comprised between around 20 µM and 0.0001 µM or between around 5 µM and 0.0001 µM or between around 1 µM and 0.0001 µM.

Those skilled in the art are aware of a variety of modifications to this assay that can be useful for measuring inhibition of stearoyl-CoA desaturase activity in microsomes or in cells by test compounds.

All of the U.S. patents, U.S. patent application publications, U.S. patent applications, foreign patents, foreign patent applications and non-patent publications referred to in this specification and/or listed in the Application Data Sheet are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A compound of formula (I):

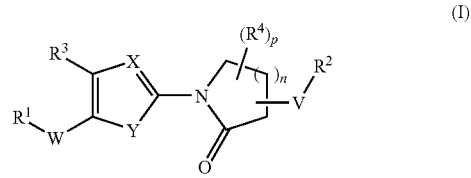

wherein:
X is CH or N;
Y is NH, N—$CH_3$, O or S;
W is —N(R)C(O)—, —C(O)N(R)— or C(O)O;
V is —N($R^5$)C(O)—, —C(O)N($R^5$)—, —OC(O)N($R^5$)—, —N($R^5$)C(O)O—, —N($R^5$)C(O)N($R^5$)—, —O—, —S—, —N($R^5$)—, —S(O)$_t$—, —N($R^5$)S(O)$_t$—, —S(O)$_t$N($R^5$)—, —OS(O)$_t$N($R^5$)—, —C(O)—, —OC(O)—, —C(O)O—, —N(R)C(=N($R^{5a}$))N$R^5$—, —N($R^5$)(($R^{5a}$)N=)C—, —C(=N($R^{5a}$))N(R)—, =C($R^5$)— or a direct bond;
n is 0, 1, 2 or 3;
p is 0 or an integer from 1 to 9;
t is 1 or 2;
$R^1$ is hydrogen, alkyl, alkenyl, alkynyl, hydroxyalkyl, alkoxyalkyl, cycloalkyl, cycloalkylalkyl, aryl, aralkyl, heterocyclyl, heterocyclylalkyl, heteroaryl or heteroarylalkyl;
or $R^1$ is a multi-ring structure having 2 to 4 rings wherein the rings are independently cycloalkyl, heterocyclyl, aryl or heteroaryl and wherein some or all of the rings may be fused to each other;
$R^2$ is hydrogen, alkyl, alkenyl, alkynyl, hydroxyalkyl, alkoxyalkyl, cycloalkyl, cycloalkylalkyl, aryl, aralkyl, heterocyclyl, heterocyclylalkyl, heteroaryl or heteroarylalkyl;
or $R^2$ is a multi-ring structure having 2 to 4 rings wherein the rings are independently cycloalkyl, heterocyclyl, aryl or heteroaryl and wherein some or all of the rings may be fused to each other;
$R^3$ is hydrogen, alkyl, alkenyl, alkynyl, hydroxyalkyl, alkoxyalkyl, cycloalkyl, cycloalkylalkyl, heterocyclyl, aryl, aralkyl, heteroaryl, halo, haloalkyl, haloalkyoxy, cyano or —N($R^5$)$_2$;
each $R^4$ is independently alkyl, halo, haloalkyl, haloalkoxy, hydroxyl, hydroxyalkyl, alkoxy, —N($R^5$)$_2$, cycloalkylalkyl or aralkyl;
or two $R^4$s attached to the same carbon form an oxo while each of the remaining $R^4$s are as described above;
each $R^5$ is independently hydrogen, alkyl, aryl, heteroaryl, cycloalkyl, hydroxyalkyl, cycloalkylalkyl or aralkyl; and
$R^{5a}$ is hydrogen, alkyl, cycloalkylalkyl or cyano; or
a pharmaceutically acceptable salt thereof.

2. The compound according to claim 1, or a pharmaceutically acceptable salt thereof, wherein
V is =C($R^5$)—, —N($R^5$)$_2$— or a direct bond;
X is N or CH;
Y is S;

p is 0, 1, 2, 3, 4, or 5;
$R^1$ is hydrogen, alkyl, aryl, aralkyl, cycloalkyl, cycloalkylalkyl, heterocyclyl, heterocyclylalkyl, heteroaryl or heteroarylalkyl;
$R^2$ is hydrogen, alkyl, alkenyl, hydroxyalkyl, alkoxyalkyl, cycloalkyl, cycloalkylalkyl, aryl, aralkyl, heterocyclyl, heterocyclylalkyl, heteroaryl or heteroarylalkyl;
$R^3$ is hydrogen or alkyl; and
$R^5$ is hydrogen or alkyl.

3. The compound according to claim 1, or a pharmaceutically acceptable salt thereof, wherein
V is a direct bond;
W is —N($R^5$)C(O)— or —C(O)O—;
X is N or CH;
Y is S;
p is 0, 1, 2, 3, 4, or 5;
$R^1$ is alkyl, aryl, aralkyl, cycloalkylalkyl, heterocyclyl, heterocyclylalkyl or heteroarylalkyl;
$R^2$ is hydrogen, alkyl, hydroxyalkyl, alkoxyalkyl, cycloalkyl, cycloalkylalkyl, aryl or aralkyl;
$R^3$ is hydrogen or alkyl; and
$R^5$ is hydrogen or alkyl.

4. The compound according to claim 1, or a pharmaceutically acceptable salt thereof, wherein
V is a direct bond;
W is —N($R^5$)C(O)—;
X is N or CH;
Y is S;
p is 0, 1, 2, 3, 4, or 5;
n is 1 or 2;
$R^1$ is alkyl, aryl, aralkyl or heteroaryl;
$R^2$ is alkyl, hydroxyalkyl, alkoxyalkyl, cycloalkyl, cycloalkylalkyl, aryl or aralkyl;
$R^3$ is alkyl; and
$R^5$ is hydrogen.

5. The compound according to claim 1, wherein the compound is selected from the group consisting of:
N-Benzyl-2-(2,6-dioxo-4-phenylpiperidin-1-yl)-4-methylthiazole-5-carboxamide;
N-Benzyl-2-(3-benzyl-2-oxopiperidin-1-yl)-4-methylthiazole-5-carboxamide;
N-Benzyl-4-methyl-2-(2-oxo-3-(4-(trifluoromethyl)benzyl)piperidin-1-yl)thiazole-5-carboxamide;
N-Benzyl-2-(3-(4-fluorobenzyl)-2-oxopiperidin-1-yl)-4-methylthiazole-5-carboxamide;
N-Benzyl-4-methyl-2-(3-(4-methylbenzyl)-2-oxopiperidin-1-yl)thiazole-5-carboxamide;
N-Benzyl-2-(3-(3-fluorobenzyl)-2-oxopiperidin-1-yl)-4-methylthiazole-5-carboxamide;
N-Benzyl-2-(3-(2,5-difluorobenzyl)-2-oxopiperidin-1-yl)-4-methylthiazole-5-carboxamide;
N-Benzyl-2-(3-(4-methoxybenzyl)-2-oxopiperidin-1-yl)-4-methylthiazole-5-carboxamide;
N-Benzyl-2-(3-(hydroxy(phenyl)methyl)-2-oxopiperidin-1-yl)-4-methylthiazole-5-carboxamide;
N-Benzyl-2-(3-((5-ethylthiophen-2-yl)methylene)-2-oxopiperidin-1-yl)-4-methylthiazole-5-carboxamide;
N-Benzyl-4-methyl-2-(2-oxo-3-(pyridin-3-ylmethylene)piperidin-1-yl)thiazole-5-carboxamide;
N-Benzyl-4-methyl-2-(2-oxo-3-(3-phenylpropyl)piperidin-1-yl)thiazole-5-carboxamide;
N-Benzyl-4-methyl-2-(2-oxo-3-(pyridin-3-ylmethyl)piperidin-1-yl)thiazole-5-carboxamide;
N-Benzyl-4-methyl-2-(2-oxo-3-phenethylpiperidin-1-yl)thiazole-5-carboxamide;
N-(3-Fluorobenzyl)-4-methyl-2-(2-oxo-3-(4-(trifluoromethyl)benzyl)piperidin-1-yl)thiazole-5-carboxamide;
N-(3-Fluorobenzyl)-2-(3-(4-fluorobenzyl)-2-oxopiperidin-1-yl)-4-methylthiazole-5-carboxamide;
N-Benzyl-2-(3-(cyclopropylmethylamino)-2-oxopiperidin-1-yl)-4-methylthiazole-5-carboxamide;
N-Benzyl-4-methyl-2-(2-oxo-3-(4-(trifluoromethyl)benzylamino)piperidin-1-yl)thiazole-5-carboxamide;
N-(4-Fluorobenzyl)-4-methyl-2-(2-oxo-3-(4-(trifluoromethyl)benzyl)pyrrolidin-1-yl)thiazole-5-carboxamide;
N-(4-Fluorobenzyl)-2-(3-(4-fluorobenzyl)-2-oxopyrrolidin-1-yl)-4-methylthiazole-5-carboxamide;
2-(3-(4-(Difluoromethoxy)benzyl)-2-oxopyrrolidin-1-yl)-N-(4-fluorobenzyl)-4-methylthiazole-5-carboxamide;
N-(4-Fluorobenzyl)-4-methyl-2-(2-oxo-3-(4-(trifluoromethoxy)benzyl)pyrrolidin-1-yl)thiazole-5-carboxamide;
N-Benzyl-4-methyl-2-(2-oxo-3-(4-(trifluoromethyl)benzyl)pyrrolidin-1-yl)thiazole-5-carboxamide;
N-Benzyl-2-(3-(4-(difluoromethoxy)benzyl)-2-oxopyrrolidin-1-yl)-4-methylthiazole-5-carboxamide;
2-(3-(Cyclopropylmethyl)-2-oxopyrrolidin-1-yl)-N-(4-fluorobenzyl)-4-methylthiazole-5-carboxamide;
2-(3-(2-Cyclopropylethylamino)-2-oxopyrrolidin-1-yl)-N-(4-fluorobenzyl)-4-methylthiazole-5-carboxamide;
N-(4-Fluorobenzyl)-2-(3-(4-fluorobenzylamino)-2-oxopyrrolidin-1-yl)-4-methylthiazole-5-carboxamide;
N-(4-Fluorobenzyl)-4-methyl-2-(2-oxo-3-(3,3,3-trifluoropropylamino)pyrrolidin-1-yl)thiazole-5-carboxamide;
N-Benzyl-2-(4-benzyl-2-oxopyrrolidin-1-yl)-4-methylthiazole-5-carboxamide;
(S)-N-Benzyl-2-(4-hydroxy-2-oxopyrrolidin-1-yl)-4-methylthiazole-5-carboxamide;
(R)-N-Benzyl-2-(4-hydroxy-2-oxopyrrolidin-1-yl)-4-methylthiazole-5-carboxamide;
2-(3-(4-Fluorobenzyl)-2-oxopyrrolidin-1-yl)-4-methyl-N-(pyridin-3-ylmethyl)thiazole-5-carboxamide; 4-Methyl-2-(2-oxo-3-(4-(trifluoromethoxy)benzyl)pyrrolidin-1-yl)-N-(pyridin-3-ylmethyl)thiazole-5-carboxamide;
N-benzyl-4-methyl-2-(2-oxopyrrolidin-1-yl)thiazole-5-carboxamide;
N-(4-Fluorobenzyl)-4-methyl-2-(2-oxopyrrolidin-1-yl)thiazole-5-carboxamide;
N-benzyl-4-methyl-2-(2-oxopiperidin-1-yl)thiazole-5-carboxamide;
N-(3-fluorobenzyl)-4-methyl-2-(2-oxopiperidin-1-yl)thiazole-5-carboxamide;
2-(3-bromo-2-oxopyrrolidin-1-yl)-N-(4-fluorobenzyl)-4-methylthiazole-5-carboxamide; and
N-benzyl-2-(3-bromo-2-oxopiperidin-1-yl)-4-methylthiazole-5-carboxamide, or
a pharmaceutically acceptable salt thereof.

6. A pharmaceutical composition, comprising:
a compound of formula (I) according to claim 1, or a pharmaceutically acceptable salt thereof, and
a pharmaceutically acceptable excipient or carrier.

7. A method of inhibiting human stearoyl-CoA desaturase (hSCD) activity, comprising:
contacting a source of hSCD with a compound of claim 1 or a pharmaceutically acceptable salt thereof.

8. A method of treating a disease or condition mediated by stearoyl-CoA desaturase (SCD) in a mammal in need thereof, comprising:

administering to the mammal in need thereof a therapeutically effective amount of the compound of formula (I) according to claim 1, or a pharmaceutically acceptable salt thereof.

9. A pharmaceutical composition, comprising:
a therapeutically effective amount of the compound of claim 1, or a pharmaceutically acceptable salt thereof, in combination with a therapeutically effective amount of insulin, an insulin derivative or mimetic; an insulin secretagogue; an insulinotropic sulfonylurea receptor ligand; a PPAR ligand; an insulin sensitizer; a biguanide; an alpha-glucosidase inhibitor; GLP-1, a GLP-1 analog or mimetic; a DPPIV inhibitor; a HMG-CoA reductase inhibitor; a squalene synthase inhibitor; a FXR or LXR ligand; cholestyramine; a fibrate; nicotinic acid; or aspirin.

* * * * *